(12) United States Patent
Li et al.

(10) Patent No.: US 9,090,671 B2
(45) Date of Patent: Jul. 28, 2015

(54) MACROCYCLIC PEPTIDES

(75) Inventors: Keqiang Li, Cary, NC (US); Ahmed Mamai, Raleigh, NC (US); Michael Robert Peel, Research Triangle Park, NC (US)

(73) Assignee: Scynexis, Inc., Durham, NC (US)

( * ) Notice: Subject to any disclaimer, the term of this patent is extended or adjusted under 35 U.S.C. 154(b) by 864 days.

(21) Appl. No.: 12/479,633

(22) Filed: Jun. 5, 2009

(65) Prior Publication Data

US 2009/0312300 A1 Dec. 17, 2009

Related U.S. Application Data

(60) Provisional application No. 61/059,649, filed on Jun. 6, 2008.

(51) Int. Cl.
*A61K 31/33* (2006.01)
*C07K 7/64* (2006.01)

(52) U.S. Cl.
CPC ..................................... *C07K 7/645* (2013.01)

(58) Field of Classification Search
None
See application file for complete search history.

(56) References Cited

U.S. PATENT DOCUMENTS

| | | | |
|---|---|---|---|
| 4,703,033 | A | 10/1987 | Seebach |
| 4,771,122 | A | 9/1988 | Seebach |
| 4,798,823 | A | 1/1989 | Witzel |
| 4,814,323 | A | 3/1989 | Andrieu et al. |
| 4,885,276 | A | 12/1989 | Witzel |
| 4,996,193 | A | 2/1991 | Hewitt et al. |
| 5,948,693 | A | 9/1999 | Rich et al. |
| 5,948,755 | A | 9/1999 | Barriere et al. |
| 5,948,884 | A | 9/1999 | Luchinger |
| 5,965,527 | A | 10/1999 | Barriere et al. |
| 5,977,067 | A | 11/1999 | Evers et al. |
| 5,981,479 | A | 11/1999 | Ko et al. |
| 5,994,299 | A | 11/1999 | Barriere et al. |
| 6,444,643 | B1 | 9/2002 | Steiner et al. |
| 6,521,595 | B1 | 2/2003 | Kim et al. |
| 6,583,265 | B1 | 6/2003 | Ellmerer-Muller et al. |
| 6,924,271 | B2 | 8/2005 | Averett et al. |
| 6,927,208 | B1 | 8/2005 | Wenger |
| 7,012,066 | B2 | 3/2006 | Saksena et al. |
| 7,105,499 | B2 | 9/2006 | Carroll et al. |
| 7,196,161 | B2 | 3/2007 | Fliri et al. |
| 7,226,905 | B2 | 6/2007 | Viskov |
| 7,576,057 | B2 | 8/2009 | Scribner et al. |
| 7,718,767 | B2 | 5/2010 | Fliri et al. |
| 7,754,685 | B2 | 7/2010 | Houck |
| 8,188,052 | B2 | 5/2012 | Houck |
| 8,329,658 | B2 | 12/2012 | Houck et al. |
| 8,536,114 | B2 | 9/2013 | Li et al. |
| 8,551,952 | B2 | 10/2013 | Houck |
| 2004/0077587 | A1 | 4/2004 | Sommadossi et al. |
| 2004/0087496 | A1 | 5/2004 | Kim et al. |
| 2004/0254117 | A9 | 12/2004 | Saksena et al. |
| 2006/0089301 | A1 | 4/2006 | Fliri et al. |
| 2006/0160727 | A1 | 7/2006 | Fliri et al. |
| 2007/0078122 | A1 | 4/2007 | Bergstrom et al. |
| 2007/0173440 | A1 | 7/2007 | Houck |
| 2007/0275884 | A1 | 11/2007 | Hijikata et al. |
| 2008/0171699 | A1 | 7/2008 | Scribner et al. |
| 2008/0255038 | A1 | 10/2008 | Hopkins et al. |
| 2009/0298751 | A1 | 12/2009 | Houck et al. |
| 2009/0306033 | A1 | 12/2009 | Li et al. |
| 2009/0312300 | A1 | 12/2009 | Li et al. |
| 2010/0062975 | A1 | 3/2010 | Houck |
| 2010/0167996 | A1 | 7/2010 | Fliri et al. |
| 2010/0173836 | A1 | 7/2010 | Li et al. |
| 2010/0173837 | A1 | 7/2010 | Hopkins |
| 2010/0227801 | A1 | 9/2010 | Hopkins |
| 2011/0144005 | A1 | 6/2011 | Li et al. |
| 2012/0264679 | A1 | 10/2012 | Fliri et al. |
| 2012/0270804 | A1 | 10/2012 | Houck |

FOREIGN PATENT DOCUMENTS

| | | |
|---|---|---|
| WO | WO 98/28328 | 7/1998 |
| WO | WO 98/28329 | 7/1998 |
| WO | WO 98/28330 | 7/1998 |
| WO | 98/49193 A1 | 11/1998 |
| WO | WO 99/32512 | 7/1999 |
| WO | 99/62540 A1 | 12/1999 |
| WO | 99/67280 A1 | 12/1999 |
| WO | WO 99/62540 A1 | 12/1999 |
| WO | WO 99/65933 | 12/1999 |
| WO | WO 99/67280 A1 | 12/1999 |
| WO | WO 00/01715 | 1/2000 |
| WO | WO 01/47883 | 5/2001 |
| WO | WO 02/057287 | 7/2002 |
| WO | WO 02/098424 | 12/2002 |
| WO | WO 03/105770 | 12/2003 |
| WO | WO 2004/007512 | 1/2004 |

(Continued)

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Anderson (Chem and Biol 10:787-797, 2003).*
Thiel (Nature Biotechnol 2:513-519, 2004).*
PCT International Search Report and Written Opinion dated Jan. 21, 2010, for International Application No. PCT/US2009/003411, filed Jun. 5, 2009.
Peel, et al., "The Discovery of Novel, Non-Immunosuppressive Cyclosporin Ethers, and Thioethers with Potent HCV Activity," AASLD Abstracts XP-002561933, Hepatology, vol. 48, No. 4, Suppl. 5, Oct. 2008, p. 1167A, Abstract 1915.

(Continued)

*Primary Examiner* — Craig Ricci
(74) *Attorney, Agent, or Firm* — Jones Day

(57) ABSTRACT

Disclosed are cyclosporine derivatives in which the 3-Sarcosine carbon and 5-Valine nitrogen are each substituted by a non-hydrogen substituent, and their use as pharmaceuticals, in particular for the treatment of hepatitis C virus.

5 Claims, No Drawings

(56) References Cited

FOREIGN PATENT DOCUMENTS

| WO | WO 2004/041221 | | 5/2004 | |
|---|---|---|---|---|
| WO | WO 2004/074270 | | 9/2004 | |
| WO | WO 2004/087714 | | 10/2004 | |
| WO | WO 2005/000308 | | 1/2005 | |
| WO | WO 2005/021028 | A1 | 3/2005 | |
| WO | WO 2005/034941 | | 4/2005 | |
| WO | WO 2005/084315 | | 9/2005 | |
| WO | 2006/005580 | A1 | 1/2006 | |
| WO | 2006/005610 | A1 | 1/2006 | |
| WO | WO 2006/005580 | * | 1/2006 | ............. A61K 38/13 |
| WO | WO 2006/005580 | A1 | 1/2006 | |
| WO | WO 2006/005610 | | 1/2006 | |
| WO | WO 2006/008556 | | 1/2006 | |
| WO | WO 2006/012078 | | 2/2006 | |
| WO | WO 2006/018725 | | 2/2006 | |
| WO | WO 2006/029912 | | 3/2006 | |
| WO | WO 2006/038088 | | 4/2006 | |
| WO | WO 2006/039668 | A2 | 4/2006 | |
| WO | WO 2006/041631 | | 4/2006 | |
| WO | WO 2006/046030 | | 5/2006 | |
| WO | WO 2006/046039 | | 5/2006 | |
| WO | WO 2006/065335 | | 6/2006 | |
| WO | WO 2006/071618 | | 7/2006 | |
| WO | WO 2006/071619 | | 7/2006 | |
| WO | WO 2007/029029 | | 3/2007 | |
| WO | WO 2007/041631 | A1 | 4/2007 | |
| WO | WO 2007/041632 | | 4/2007 | |
| WO | WO 2007/136759 | | 11/2007 | |
| WO | WO 2008/069917 | | 6/2008 | |
| WO | WO 2008/127613 | | 10/2008 | |
| WO | WO 2008/143996 | | 11/2008 | |
| WO | WO 2009/148615 | | 12/2009 | |
| WO | WO 2010/002428 | | 1/2010 | |

OTHER PUBLICATIONS

EPO Supplemental European Search Report, dated Jul. 18, 2008, for European Application No. EP 05815625.8, filed Sep. 30, 2005.

EPO European Examination Report, Communication pursuant to Article 94(3) EPC, dated Sep. 8, 2008, for European Application No. EP 06816230.4, filed Oct. 2, 2006.

ISA/US PCT International Search Report and Written Opinion dated Feb. 6, 2007, for International Application No. PCT/US05/35533, filed Sep. 30, 2005.

ISA/US PCT International Preliminary Report on Patentability dated Apr. 3, 2007, for International Application No. PCT/US05/35533, filed Sep. 30, 2005.

ISA/US PCT International Search Report and Written Opinion dated Jan. 19, 2007, for International Application No. PCT/US06/038822, filed Oct. 2, 2006.

ISA/US PCT International Preliminary Report on Patentability dated Apr. 1, 2008, for International Application No. PCT/US06/038822, filed Oct. 2, 2006.

ISA/US PCT International Search Report and Written Opinion dated Oct. 31, 2007, for International Application No. PCT/US2006/038823, filed Oct. 2, 2006.

ISA/US PCT International Preliminary Report on Patentability dated Apr. 1, 2008, for International Application No. PCT/US2006/038823, filed Oct. 2, 2006.

ISA/US PCT International Search Report and Written Opinion dated Jul. 30, 2008, for International Application No. PCT/US2008/004626, filed Apr. 10, 2008.

ISA/US PCT International Preliminary Report on Patentability dated Oct. 13, 2009, for International Application No. PCT/US2008/004626, filed Apr. 10, 2008.

ISA/US PCT International Search Report and Written Opinion dated Oct. 27, 2009, for International Application No. PCT/US2009/003410, filed May 18, 2007.

ISA/US PCT International Search Report and Written Opinion dated May 5, 2010, for International Application No. PCT/US10/20316, filed Jan. 7, 2010.

U.S.P.T.O. Non-Final Office action dated Dec. 11, 2007, in U.S. Appl. No. 11/386,291, filed Mar. 21, 2006.

U.S.P.T.O. Final Office action dated Jul. 16, 2008, in U.S. Appl. No. 11/386,291, filed Mar. 21, 2006.

Baumgrass et al., 2004, "Substitution in Position 3 of Cyclosporin a Abolishes the Cyclophilin-mediated Gain-of-function Mechanism but Not Immunosuppression," *Journal of Biological Chemistry*, vol. 279(4):2470-2479.

Billich et al., 1995, "Mode of Action of SDZ NIM 811, a Nonimmunosuppressive Cyclosporin a Analog with Activity Against Human Immunodeficiency Virus (HIV) Type 1: Interference with HIV Protein-Cyclophilin a Interactions," *Journal of Virology*, vol. 69(4):2451-2461.

Biswal et al., 2005, "Crystal Structures of the RNA-dependent RNA Polymerase Genotype 2a of Hepatitis C Virus Reveal Two Conformations and Suggest Mechanisms of Inhibition by Non-Nucleoside Inhibitors," *J. Biol. Chem.*, vol. 280:18202-18210.

Borel et al., 1977, "Effects of the New Anti-Lymphocytic Peptide Cyclosporin A in Animals," *Immunology*, vol. 32:1017-1025.

Chan et al., 2004, "Discovery of Thiophene-2-Carboxylic Acids as Potent Inhibitors of HCV NS5B Polymerase and HCV Subgenomic RNA Replication. Part 1: Sulfonamides," *Bioorganic & Medical Chemistry Letters*, 14:793-796.

Chan et al., 2004, "Discovery of Thiophene-2-Carboxylic Acids as Potent Inhibitors of HCV NS5B Polymerase and HCV Subgenomic RNA Replication. Part 2: Tertiary Amides," *Bioorganic & Medicinal Chemistry Letters*, 14:797-800.

Cotler, Scott J., et al., 2003-04, "A Pilot Study of the Combination of Cyclosporin A and Interferon Alfacon-1 for the Treatment of Hepatitis C in Previous Nonresponder Patients," *Journal of Clinical Gastroenterology*, vol. 36(4):352-355.

Debio Pharm Press Release, New Data Presented on Debiopharm's Debio-25 at the 11th International Symposium on Hepatitis C Virus and Related Viruses in Heidelberg, Germany, Oct. 6, 2004.

Dhanak et al., 2002, "Identification and Biological Characterization of Heterocyclic Inhibitors of the Hepatitis C Virus RNA-Dependent RNA Polymerase," *Journal of Biological Chemistry*, vol. 277(41):38322-38327.

DiMarco et al., 2005, "Interdomain Communication in Hepatitis C Virus Polymerase Abolished by Small Molecule Inhibitors Bound to a Novel Allosteric Site," *Journal of Biological Chemistry*, vol. 280(33):29765-29770.

Evers et al., 2003, "Synthesis of Non-Immunosuppressive Cyclophilin-Binding Cyclosporin a Derivatives as Potential Anti-HIV-1 Drugs," *Bioorganic & Medicinal Chemistry Letters*, vol. 13:4415-4419.

Gu et al., 2003, "Arresting Initiation of Hepatitis C Virus RNA Synthesis Using Heterocyclic Derivatives," *Journal of Biological Chemistry*, vol. 278(19):16602-16607.

Hansson et al., 2004, "The Nonimmunosuppressive Cyclosporin Analogs NIM811 and UNIL025 Display Nanomolar Potencies on Permeability Transition in Brain Derived Mitochondria," *Journal of Bioenergetics and Biomembranes*, vol. 36(4):407-413.

Harper et al., 2005, "Development and Preliminary Optimization of Indole-N-Acetamide Inhibitors of Hepatitis C Virus NS5B Polymerase," *J. Med. Chem.*, vol. 48:1314-1317.

Harper et al., 2005, "Potent Inhibitors of Subgenomic Hepatitis C Virus RNA Replication Through Optimization of Indole-N-Acetamide Allosteric Inhibitors of the Viral NS5B," *J. Med. Chem.*, vol. 48:4547-4557.

Hopkins et al., 2009, "Safety, Plasma Pharmacokinetics, and Anti-Viral Activity of SCY-635 in Adult Patients with Chronic Hepatitis C virus Infection," *Journal of Hepatology*, vol. 50(Suppl. 1):S36 & 44th Annual meeting of the European Association for the Study of the Liver, Copenhagen, Denmark, Apr. 22-26, 2009.

Horsmans et al., 2004, "Isatoribine, A Toll-Like Receptor 7 Agonist, Significantly Reduced Plasma Viral Load in a Clinical Proof-of-Concept Study in Patients with Chronic Hepatitis C Virus Infection," *Hepatology*, vol. 40:(4), Suppl. 1, Oct. 2004, 282A, No. 270.

Hubler et al., 2000, Synthetic Routes to NEtXaa4-Cyclosporin A Derivatives as Potential Anti-HIV I Drugs, *Tetrahedron Letters*, vol. 41(37):7193-7196.

(56) References Cited

OTHER PUBLICATIONS

Inoue et al., 2003, "Combined Interferon Alpha2b and Cyclosporin A in the Treatment of Chronic Hepatitis C: Controlled Trial," *Journal of Gastroenterology*, Springer Verlag, Tokyo, JP, vol. 38(6):567-572.

Inoue et al., 2005, "Interferon Combined with Cyclosporin Treatment as an Effective Countermeasure Against Hepatitis C Virus Recurrence in Liver Transplant patients with End-Stage Hepatitis C Virus Related Disease," *Transplantation Proceedings*, vol. 37(2):1233-1234.

Kallen et al., 1997, "12 Cyclosporins: Recent Developments in Biosynthesis, Pharmacology and Biology, and Clinical Applications," *Biotechnology*, 2$^{nd}$ Ed. Completely Revised Edition, vol. 7, pp. 535-591.

Klumpp et al., 2008, "2-Deoxy-4'-Azido Nucleoside Analogs Are Highly Potent Inhibitors of Hepatitis C Virus Replication Despite the Lack of 2'-α-Hydroxyl Groups," *J. Biol. Chem.*, vol. 283(4):2167-2175.

Ko et al., 1997, "Solid-Phase Total Synthesis of Cyclosporine Analogues," *Helvetica Chimica Acta*, vol. 80:695-705.

Lamarre et al., 2003, "An NS3 Protease Inhibitor with Antiviral Effects in Humans Infected with Hepatitis C Virus," *Nature*, vol. 426:186-189.

LaPlante et al., 2004, "Binding Mode Determination of Benzimidazole Inhibitors of the Hepatitis C Virus RNA Polymerase by a Structure and Dynamics Strategy," *Angew. Chem. Int.*, Ed. Engl., vol. 32:4306-4311.

Li et al., 2007, "Allosteric Inhibitors of Hepatitis C Polymerase: Discovery of Potent and Orally Bioavailable Carbon-Linked Dihydropyrones," *J. Med. Chem.* vol. 50(17):3969-3972.

Lin et al., 2005, "In Vitro Studies of Cross-Resistance Mutations Against Two Hepatitis C Virus Serine Protease Inhibitors, VX-950 and BILN 2061," *Journal of Biological Chemistry*, vol. 280(44):36784-36791.

Love et al., 2003, "Crystallographic Identification of a Noncompetitive Inhibitor Binding Site on the Hepatitis C Virus NS5B RNA Polymerase Enzyme," *Journal of Virology*, vol. 77(13):7575-7581.

Nakagawa et al., 2004, "Specific Inhibition of Hepatitis C Virus Replication by Cyclosporin A," *Biochem. Biophys. Res. Commun.*, vol. 313:42-47.

Nguyen et al., 2003, "Resistance Profile of a Hepatitis C Virus RNA-Dependent RNA Polymerase Benzothiadiazine Inhibitor," *Antimicrobial Agents and Chemotherapy*, vol. 47(11):3525-3530.

Olsen et al., 2004, "A 7-Deaza-Adenosine Analog is a Potent and Selective Inhibitor of Hepatitis C Virus Replication with Excellent Pharmacokinetic Properties," *Antimicrobial Agents and Chemotherapy*, vol. 48(10):3944-3953.

Papageorgiou et al., 1997, "Conformational Control of Cyclosporin through Substitution of the N-5 Position. A New Class of Cyclosporin Antagonists," *Bioorganic & Medicinal Chemistry* (1):187-192.

Randall et al., 2003, "Clearance of Replicating Hepatitis C Virus Replicon RNAs in Cell Culture by Small Interfering RNAs," *PNAS*, vol. 100(1):235-240.

Ruegger et al., 1976, "Cyclosporin A, a Peptide Metabolite from *Trichoderma polysporum* (Link ex Pers.) Rifai, with a Remarkable Immunosuppressive Activity," *Helvetica Chimica Acta*, vol. 59(4) No. 112, pp. 1075-1092.

Schetter et al., 2004, "Toll-Like Receptors Involved in the Response to Microbial Pathogens: Development of Agonists for Toll-Like Receptor 9," *Current Opinion in Drug Discovery & Development*, vol. 7(2):204-210.

Scynexis Inc. Press Release, Scynexis' SCY-635 Demonstrates Clinically Relevant Single-agent Results in a Phase 1b Study in Adults with HCV (Results presented in an oral presentation at EASL; Phase 2 studies to be initiated in 2H09), Research Triangle Park, NC, USA, Apr. 24, 2009.

Shimotohno et al., 2004, "Inhibitory Role of Cyclosporin a and Its Derivatives on Replication of Hepatitis C Virus," American Transplant Congress, Abstract No. 648 (American Journal of Transplantation, 4(s8):1-653.

Simmonds, P., 2001, "The Origin and Evolution of Hepatitis Viruses in Humans," *Journal of General Virology*, vol. 82:693-712.

Simmonds, P., 2004, "Genetic Diversity and Evolution of Hepatitis C Virus—15 Years On," *Journal of General Virology*, vol. 85:3173-3188.

Summa, V., 2005, "VX-950 Vertex/Mitsubishi," *Current Opinion in Investigational Drugs*, vol. 6(8):831-837.

Takeda et al., 2003, "Toll-Like Receptors," *Annual Review Immunology*, vol. 21:335-376.

Tomei et al., 2003, "Mechanisms of Action and Antiviral Activity of Benzimidazole-Based Allosteric Inhibitors of the Hepatitis C Virus RNA-Dependent RNA Polymerase," *Journal of Virology*, vol. 77(24)13225-13231.

Tomei et al., 2004, "Characterization of the Inhibition of Hepatitis C Virus RNA Replication by NonNucleosides," *Journal of Virology*, vol. 78(2):938-946.

Traber et al., 1987, "Novel Cyclosporins from *Tolypocladium inflatum*. The Cyclosporins K-Z," *Helveltica Chimica Acta*, vol. 70, No. 1, pp. 13-36.

Wang et al., 2003, "Non-Nucleoside Analogue Inhibitors Bind to an Allosteric Site on HCV NS5B Polymerase," *Journal of Biological Chemistry*, vol. 278(11):9489-9495.

Watashi et al., 2003, "Cyclosporin A Suppresses Replication of Hepatitis C Virus Genome in Cultured Hepatocytes," *Hepatology*, vol. 38:1282-1288.

Watashi et al., 2005, "Cyclophilin B is a Functional Regulator of Hepatitis C Virus RNA Polymerase," *Molecular Cell*, vol. 19: 111-122.

Watashi et al., 2005, "Current Approaches for Developing New Anti-HCV Agents and Analyses of HCV Replication Using Anti-HCV Agents," *Uirusu*, vol. 55(1):105-110.

Xia et al., 2005, "Inhibitory Effect of Cyclosporine A on Hepatitis B Virus Replication in Vitro and its Possible Mechanisms," *Hepatobiliary & Pancreatic Diseases International*, vol. 4(1):18-22.

ISA/EPO PCT International Preliminary Report on Patentability mailed Dec. 16, 2010, for International Application No. PCT/US2009/003410, filed Jun. 5, 2009.

ISA/EPO PCT International Preliminary Report on Patentability mailed Dec. 16, 2010, for International Application No. PCT/US2009/003411, filed Jun. 5, 2009.

USPTO nonfinal Office Action mailed Jan. 14, 2011, for U.S. Appl. No. 11/479,623, filed Jun. 5, 2009.

Response to Rules 161(1) and 162 EPC, filed Feb. 23, 2011, for European Application No. 09773881.9.

Carry et al., 2004, "Semisynthetic Di- and Tri-Functionalized Non-Immunosuppressive Cyclosporin A Derivatives as Potential Anti-HIV 1 Drugs," Synlett No. 2:316-320.

Peel et al., "The Discovery of Novel, Non-Immunosuppressive Cyclosporin Ethers, and Thioethers with Potent HCV Activity," Aasld Abstracts XP-002561933, Hepatology, 48(4), Suppl. S, Oct. 2008, p. 1167A, Abstract 1915.

Sakamoto et al., "Specific Inhibition of Hepatitis C Virus Replication by Cyclosporin A," Gastroenterology, 2004, vol. 126(4), p. A-764 (Abstract T1674).

* cited by examiner

MACROCYCLIC PEPTIDES

RELATED APPLICATIONS

This application claims the benefit of priority to U.S. Provisional Application No. 61/059,649, filed on Jun. 6, 2008, entitled "Novel Macrocyclic Peptides," the entire contents of which is incorporated herein by reference.

FIELD OF THE INVENTION

Disclosed herein are novel cyclosporine derivatives, compositions containing them, processes for their preparation, intermediates in their synthesis, and their use as therapeutics, for example, as antiviral agents.

BACKGROUND OF THE INVENTION

In 1989, a main causative virus of non-A non-B post-transfusion hepatitis was found and named hepatitis C virus (HCV). Since then, several types of hepatitis viruses have been found besides type A, type B and type C, wherein hepatitis caused by HCV is called hepatitis C. The patients infected with HCV are considered to involve several percent of the world population, and the infection with HCV characteristically becomes chronic.

HCV is an envelope RNA virus, wherein the genome is a single strand plus-strand RNA, and belongs to the genus *Hepacivirus* of Flavivirus (from The International Committee on Taxonomy of Viruses, International Union of Microbiological Societies). Other hepaciviruses, for example, hepatitis B virus (HBV), which is a DNA virus, is eliminated by the immune system, and the infection with this virus ends in an acute infection, with the exception of neonates and infants having yet immature immunological competence. In contrast, HCV somehow avoids the immune system of the host due to an unknown mechanism. Once infected with this virus, even an adult having a mature immune system frequently develops persistent infection.

When chronic hepatitis is associated with the persistent infection with HCV, it advances to cirrhosis or hepatic cancer at a high rate. Enucleation of tumor by operation does not help appreciably, because the patient often develops recurrent hepatic cancer due to the sequela inflammation in non-cancerous parts.

Thus, an effective therapeutic method of treating or controlling hepatitis C is desired. Apart from the symptomatic therapy to suppress inflammation with an anti-inflammatory agent, there is a demand for the development of a therapeutic agent that reduces HCV to a low level free from inflammation and that eradicates HCV. An optimal therapeutic agent would provide a virologic response classified as a "sustained virologic response," which is defined as undetectable levels of virus in blood six months or more after completing hepatitis C therapy.

At present, a treatment with interferon, as a single agent or in combination with ribavirin, is the only effective method known for the eradication of HCV. However, interferon can eradicate the virus in only about one-third of the patient population. For the rest of the patients, it has no effect or provides only a temporary effect. Therefore, there is a need for an anti-HCV drug to be used in the place of or concurrently with interferon.

Cyclosporine A is well known for its immunosuppressive activity and a range of therapeutic uses, including antifungal, anti-parasitic, and anti-inflammatory as well as anti-HIV activity. Cyclosporine A and certain derivatives have been reported as having anti-HCV activity, see Watashi et al., 2003, *Hepatology* 38:1282-1288, Nakagawa et al., 2004, *Biochem. Biophys. Res. Commun.* 313:42-7, and Shimotohno and K. Watashi, 2004, American Transplant Congress, Abstract No. 648 (American Journal of Transplantation 2004, Volume 4, Issue s8, Pages 1-653). Cyclosporine derivatives having HCV activity are known from International Publication Nos. WO2005/021028, WO2006/039668 and WO2006/038088. Cyclosporines in which the 5-Valine nitrogen is substituted by a non-hydrogen substituent are known from Papageorgiou et al, 1997, *Bioorganic & Medicinal Chemistry*, 5(1): 187-192.

SUMMARY OF THE INVENTION

In one aspect, provided herein are cyclosporine derivatives of general formula (I):

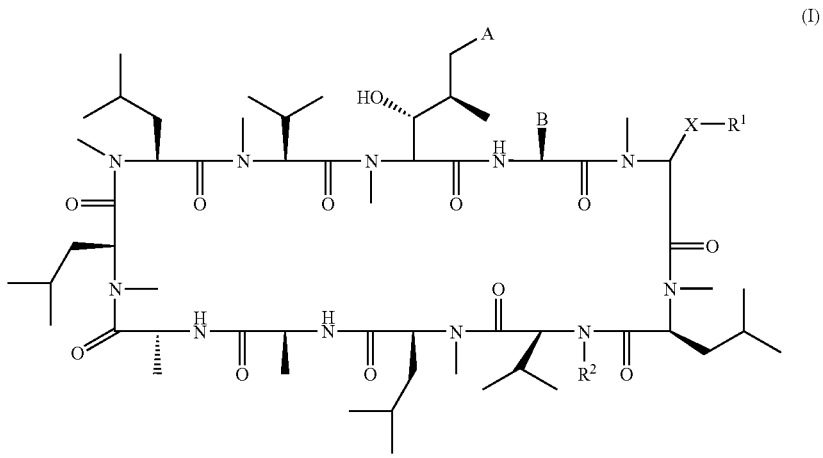

wherein:

A represents (E) —CH=CHR or —CH$_2$CH$_2$R, wherein R represents methyl, —CH$_2$SH, —CH$_2$(thioalkyl), —CH$_2$(carboxyl), —CH$_2$(alkoxycarbonyl), carboxyl or alkoxycarbonyl;

B represents methyl, ethyl, 1-hydroxyethyl, isopropyl or n-propyl;

$R^1$ represents:

straight- or branched-chain alkyl containing from one to six carbon atoms, optionally substituted by one or more groups $R^3$ which may be the same or different;

straight- or branched-chain alkenyl containing from two to six carbon atoms optionally substituted by one or more groups which may be the same or different selected from the group consisting of halogen, hydroxyl, amino, N-monoalkylamino and N,N-dialkylamino;

straight- or branched-chain alkynyl containing from two to six carbon atoms, optionally substituted by one or one or more groups which may be the same or different selected from the group consisting of halogen, hydroxyl, amino, N-monoalkylamino and N,N-dialkylamino;

cycloalkyl containing from three to six carbon atoms optionally substituted by one or more groups which may be the same or different selected from the group consisting of halogen, hydroxyl, amino, N-monoalkylamino and N,N-dialkylamino; or straight- or branched-chain alkoxycarbonyl containing from two to six carbon atoms;

$R^2$ represents:

straight- or branched-chain alkyl containing from one to six carbon atoms, optionally substituted by one or more groups $R^{41}$ which may be the same or different;

straight- or branched-chain alkenyl containing from two to six carbon atoms, optionally substituted by one or more groups $R^{42}$ which may be the same or different;

straight- or branched-chain alkynyl containing from two to six carbon atoms, optionally substituted by one or more groups which may be the same or different selected from the group consisting of halogen, hydroxyl, amino, N-monoalkylamino and N,N-dialkylamino;

cycloalkyl containing from three to six carbon atoms, optionally substituted by one or more groups which may be the same or different selected from the group consisting of halogen, hydroxyl, amino, N-monoalkylamino and N,N-dialkylamino; or straight- or branched-chain alkoxycarbonyl containing from two to six carbon atoms;

X represents —S($=$O)$_n$— or oxygen, wherein n is zero, one or two;

$R^3$ is selected from the group consisting of halogen, hydroxyl, alkoxy, carboxyl, alkoxycarbonyl, —NR$^5$R$^6$, —NR$^7$(CH$_2$)$_m$NR$^5$R$^6$, cycloalkyl and phenyl, which phenyl is optionally substituted by from one to five groups which may be the same or different selected from the group consisting of alkyl, haloalkyl, halogen, hydroxyl, alkoxy, amino, N-alkylamino, N,N-dialkylamino, carboxyl and alkoxycarbonyl; or $R^3$ is a carbon-linked saturated or unsaturated heterocyclic ring containing from four to six ring atoms, which ring may contain one or two heteroatoms which may be the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino or N,N-dialkylamino;

$R^{41}$ represents;

halogen, hydroxyl, —OR$^8$, carboxyl, alkoxycarbonyl, —NR$^5$R$^6$, —NR$^7$(CH$_2$)$_m$NR$^5$R$^6$, formyl, —C($=$O)R$^8$, —S(O)$_p$R$^8$ wherein p is zero, one or two;

phenyl optionally substituted by from one to five groups which may be the same or different selected from the group consisting of alkyl, haloalkyl, halogen, hydroxyl, alkoxy, amino, N-alkylamino, N,N-dialkylamino, carboxyl and alkoxycarbonyl; or cycloalkyl containing from three to six carbon atoms optionally substituted by one or more groups which may be the same or different selected from the group consisting of halogen, hydroxyl, amino, N-monoalkylamino and N,N-dialkylamino;

or $R^{41}$ represents a carbon-linked saturated or unsaturated heterocyclic ring containing from four to six ring atoms, which ring contains from one to three heteroatoms which may be the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino and N,N-dialkylamino;

$R^{42}$ represents:

halogen, hydroxyl, —NR$^5$R$^6$, —OR$^8$, carboxyl, alkoxycarbonyl, —C($=$O)NR$^5$R$^6$, formyl, —C($=$O)R$^8$, —S(O)$_n$R$^8$, —NR$^7$(CH$_2$)$_m$NR$^5$R$^6$;

phenyl optionally substituted by from one to five groups which may be the same or different selected from the group consisting of alkyl, haloalkyl, halogen, hydroxyl, alkoxy, amino, N-alkylamino, N,N-dialkylamino, carboxyl and alkoxycarbonyl; or cycloalkyl containing from three to six carbon atoms optionally substituted by one or more groups which may be the same or different selected from the group consisting of halogen, hydroxyl, amino, N-monoalkylamino and N,N-dialkylamino;

or $R^{42}$ is a carbon-linked saturated or unsaturated heterocyclic ring containing from four to six ring atoms, which ring contains from one to three heteroatoms which may be the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino and N,N-dialkylamino;

$R^5$ and $R^6$ which may be the same or different, each represent:

hydrogen;

straight- or branched-chain alkyl containing from one to six carbon atoms;

straight- or branched-chain alkenyl or alkynyl containing from two to four carbon atoms;

cycloalkyl containing from three to six carbon atoms optionally substituted by straight- or branched-chain alkyl containing from one to six carbon atoms;

or $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, phenyl and benzyl;

$R^7$ represents hydrogen, straight- or branched-chain alkyl containing from one to six carbon atoms, cyano or alkylsulfonyl;

$R^8$ represents:

straight- or branched-chain alkyl containing from one to six carbon atoms; aryl optionally substituted by from one to five groups which may be the same or different selected from the group consisting of alkyl, haloalkyl, halogen, hydroxyl, alkoxy, amino, N-alkylamino and N,N-dialkylamino;

heteroaryl optionally substituted by from one to five groups which may be the same or different selected from the group consisting of alkyl, haloalkyl, halogen, hydroxyl, alkoxy, amino, N-alkylamino and N,N-dialkylamino;

aralkyl, wherein the aryl ring is optionally substituted by from one to five groups which may be the same or different selected from the group consisting of halogen, amino, N-alkylamino, N,N-dialkylamino, alkoxy and haloalkyl, wherein the alkylene group contains one to three carbon atoms; or heteroarylalkyl wherein the heteroaryl ring is optionally substituted by halogen, amino, N-alkylamino, N,N-dialkylamino, alkoxy and haloalkyl, wherein the alkylene group contains one to three carbon atoms;

m is an integer from one to four;

and pharmaceutically acceptable salts and solvates thereof.

In another aspect, provided herein are compounds of general formula (I) wherein:

A represents (E) —CH═CHR or —CH$_2$CH$_2$R, wherein R represents methyl, —CH$_2$SH, —CH$_2$(thioalkyl), —CH$_2$(carboxyl) or —CH$_2$(alkoxycarbonyl);

B represents methyl, ethyl, 1-hydroxyethyl, isopropyl or n-propyl;

$R^1$ represents:
straight- or branched-chain alkyl containing from one to six carbon atoms, optionally substituted by one or more groups $R^3$ which may be the same or different;
straight- or branched-chain alkenyl containing from two to six carbon atoms, optionally substituted by one or more groups which may be the same or different selected from the group consisting of halogen, hydroxyl, amino, N-monoalkylamino and N,N-dialkylamino;
straight- or branched-chain alkynyl containing from two to six carbon atoms, optionally substituted by one or one or more groups which may be the same or different selected from the group consisting of halogen, hydroxyl, amino, N-monoalkylamino and N,N-dialkylamino;
cycloalkyl containing from three to six carbon atoms, optionally substituted by one or more groups which may be the same or different selected from the group consisting of halogen, hydroxyl, amino, N-monoalkylamino and N,N-dialkylamino; or
straight- or branched-chain alkoxycarbonyl containing from two to six carbon atoms;

$R^2$ represents:
straight- or branched-chain alkyl containing from one to six carbon atoms, optionally substituted by one or more groups $R^4$ which may be the same or different;
straight- or branched-chain alkenyl containing from two to six carbon atoms, optionally substituted by one or more groups which may be the same or different selected from the group consisting of halogen, hydroxyl, amino, N-monoalkylamino and N,N-dialkylamino;
straight- or branched-chain alkynyl containing from two to six carbon atoms substituted by one or more groups which may be the same or different selected from the group consisting of halogen, hydroxyl, amino, N-monoalkylamino and N,N-dialkylamino;
cycloalkyl containing from three to six carbon atoms, optionally substituted by one or more groups which may be the same or different selected from the group consisting of halogen, hydroxyl, amino, N-monoalkylamino and N,N-dialkylamino;
or straight- or branched-chain alkoxycarbonyl containing from two to six carbon atoms;

X represents —S(═O)$_n$— or oxygen, wherein n is zero, one or two;

$R^3$ is selected from the group consisting of halogen, hydroxyl, alkoxy, carboxyl, alkoxycarbonyl, —NR$^5$R$^6$ and —NR$^7$(CH$_2$)$_m$NR$^5$R$^6$, cycloalkyl and phenyl optionally substituted by from one to five groups which may be the same or different selected from the group consisting of alkyl, haloalkyl halogen, hydroxyl, alkoxy, amino, N-alkylamino, N,N-dialkylamino, carboxyl and alkoxycarbonyl; or $R^3$ is a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, halogen, alkoxy, amino, carboxyl and alkyl substituted by amino, N-alkylamino or N,N-dialkylamino;

$R^4$ is selected from the group consisting of halogen, hydroxyl, alkoxy, carboxyl, alkoxycarbonyl, —NR$^5$R$^6$, —NR$^7$N(CH$_2$)$_m$R$^5$R$^6$ and phenyl optionally substituted by from one to five groups which may be the same or different selected from the group consisting of alkyl, haloalkyl halogen, hydroxyl, alkoxy, amino, N-alkylamino, N,N-dialkylamino, carboxyl and alkoxycarbonyl; or $R^4$ is a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, halogen, alkoxy, amino, carboxyl and alkyl substituted by amino, N-alkylamino or N,N-dialkylamino;

$R^5$ and $R^6$, which may be the same or different, each represent:
hydrogen;
straight- or branched-chain alkyl containing from one to six carbon atoms;
straight- or branched-chain alkenyl or alkynyl containing from two to four carbon atoms; or
cycloalkyl containing from three to six carbon atoms, optionally substituted by straight- or branched-chain alkyl containing from one to six carbon atoms;
or $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, phenyl and benzyl;

$R^7$ represents hydrogen, straight- or branched-chain alkyl containing from one to six carbon atoms, cyano or alkylsulfonyl;

m is an integer from one to four;

or a pharmaceutically acceptable salt or solvate thereof.

In another aspect provided herein is a process for the preparation of a compound of formula (I), as disclosed herein.

In certain cases the substituents A, B, $R^1$ and $R^2$ may contribute to optical and/or stereoisomerism. All such forms are embraced by the present invention.

Mention may be made, as examples of pharmaceutically acceptable salts, of the salts with alkali metals, e.g., sodium, potassium or lithium, or with alkaline-earth metals, e.g., magnesium or calcium, the ammonium salt or the salts of nitrogenous bases, e.g., ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine.

DETAILED DESCRIPTION OF THE PREFERRED EMBODIMENTS

Definitions

When referring to the compounds and complexes of the invention, the following terms have the following meanings unless indicated otherwise.

"Cyclosporine" refers to any cyclosporine compound known to those of skill in the art, or a derivative thereof. See e.g., Ruegger et al., 1976, *Helv. Chim. Acta.* 59:1075-92; Borel et al., 1977, *Immunology* 32:1017-25; the contents of which are hereby incorporated by reference in their entireties. Exemplary compounds disclosed herein are cyclosporine derivatives. Unless noted otherwise, a cyclosporine described herein is a cyclosporine A, and a cyclosporine derivative described herein is a derivative of cyclosporine A.

The cyclosporine nomenclature and numbering systems used hereafter are those used by J. Kallen et al., "Cyclosporins: Recent Developments in Biosynthesis, Pharmacology and Biology, and Clinical Applications," *Biotechnology*, second edition, H.-J. Rehm and G. Reed, ed., 1997, p 535-591 and are shown below:

Position Amino Acid in Cyclosporine A
1 N-Methyl-butenyl-threonine (MeBmt)
2 [alpha]-aminobutyric acid (Abu)
3 Sarcosine (Sar)
4 N-Methyl-leucine (MeLeu)
5 Valine (Val)
6 N-Methyl-leucine (MeLeu)
7 Alanine (Ala)
8 (D)-Alanine [(D)-Ala]
9 N-Methyl-leucine (MeLeu)
10 N-Methyl-leucine (MeLeu)
11 N-Methyl-valine (MeVal)

This corresponds to the saturated ring carbon atoms in the compounds of formula (I) as shown below:

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl, and the like. The term "lower alkyl" refers to alkyl groups having 1 to 6 carbon atoms.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=$CH_2$), n-propenyl (—$CH_2$CH=$CH_2$), isopropenyl (—C($CH_3$)=$CH_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CH$CH_2$— and —C($CH_3$)=CH— and —CH=C($CH_3$)—), and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—$CH_2$C≡CH), and the like.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"N-Alkylamino" refers to the group alkyl-NR'—, wherein R' is selected from hydrogen and alkyl.

"Alkylsulfonyl" refers to a radical —S(=O)$_2$alkyl, where alkyl is as defined herein.

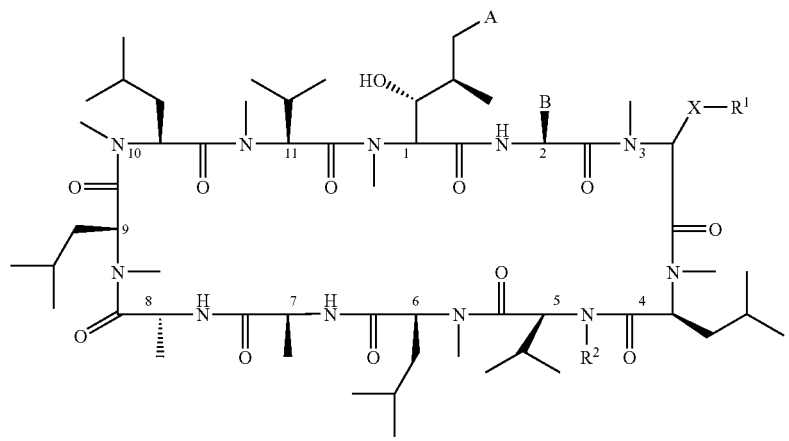

"Alkoxycarbonyl" refers to a radical —C(=O)-alkoxy, where alkoxy is as defined herein.

"Amino" refers to the radical —NH$_2$.

"Aralkyl" refers to alkyl substituted by aryl, where alkyl and aryl are as defined herein. Particular non-limiting aralkyl groups include benzyl (—CH$_2$Ph), phenethyl (—CH$_2$CH$_2$Ph), and the like.

"Aryl" refers to an optionally substituted aromatic hydrocarbon radical, for example phenyl.

"Arylamino" refers to the group aryl-NR'—, wherein R' is selected from hydrogen, aryl and heteroaryl.

"Bmt" refers to 2(S)-amino-3(R)-hydroxy-4(R)-methyl-6 (E)-octenoic acid.

"Carboxyl" refers to the radical —C(=O)OH.

"N,N-Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Formyl" refers to the radical —C(=O)H.

"Halogen" or "halo" refers to chloro, bromo, fluoro or iodo.

"Heteroaryl" refers to an optionally substituted saturated or unsaturated heterocyclic radical. Generally the heterocyclic ring contains from 4 to 7 ring atoms, e.g., 5 or 6 ring atoms. Examples of heteroaryl include thienyl, furyl, pyrrolyl, oxazinyl, thiazinyl, pyrazinyl, pyrimidinyl, pyridazinyl, thiazolyl, oxazolyl, imidazolyl, morpholinyl, pyrazolyl and tetrahydrofuryl.

"Hydroxyl" refers to the radical —OH.

"Thioalkyl" refers to the group —SR where R is alkyl. Examples include, but are not limited to, methylthio, ethylthio, propylthio, butylthio, and the like.

"Pharmaceutically acceptable salt" refers to any salt of a compound disclosed herein which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium, and the like, and when the compound contains a basic functionality, salts of non-toxic organic or inorganic acids, such as hydrohalides, e.g., hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethanedisulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations, and the like.

"Solvate" refers to a compound of the present invention, or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413-447, *Angew. Chem.*, Int. Ed. Engl. 5:385-414 (errata: *Angew. Chem.*, Int. Ed. Engl. 5:511); Prelog and Helmchen, 1982, *Angew. Chem.* 94:614-631, *Angew. Chem.* Int. Ed. Engl. 21:567-583; Mata and Lobo, 1993, *Tetrahedron. Asymmetry* 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds disclosed herein may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides stereoisomers of the compounds disclosed herein, upon treatment with base.

In certain embodiments, the compounds of the invention are "stereochemically pure". A stereochemically pure compound or has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

"Sarcosine" or "Sar" refers to the amino acid residue known to those of skill in the art having the structure —N(Me) $CH_2C(=O)$—. Those of skill in the art might recognize sarcosine as N-methyl glycine.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a monkey such as a cynomolgous monkey, a chimpanzee and a human), and more preferably a human. In another embodiment, the subject is a farm animal (e.g., a horse, a cow, a pig, etc.) or a pet (e.g., a dog or a cat). In a preferred embodiment, the subject is a human.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound disclosed herein. In certain other embodiments, the term "therapeutic agent" refers does not refer to a compound of disclosed herein. Preferably, a therapeutic agent is an agent that is known to be useful for, or has been or is currently being used for the treatment, management, prevention, or amelioration of a disorder or one or more symptoms thereof.

"Therapeutically effective amount" means an amount of a compound or complex or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound disclosed herein. In certain other embodiments, the term "prophylactic agent" does not refer a compound of the invention. Preferably, a prophylactic agent is an agent which is known to be useful for, or has been or is currently being used to prevent or impede the onset, development, progression and/or severity of a disorder.

As used herein, the terms "prevent", "preventing" and "prevention" refer to the prevention of the recurrence, onset, or development of one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the phrase "prophylactically effective amount" refers to the amount of a therapy (e.g., prophylactic agent) which is sufficient to result in the prevention of the development, recurrence or onset of one or more symptoms associated with a disorder, or to enhance or improve the prophylactic effect(s) of another therapy (e.g., another prophylactic agent).

The term "label" refers to a display of written, printed or graphic matter upon the immediate container of an article, for example the written material displayed on a vial containing a pharmaceutically active agent.

The term "labeling" refers to all labels and other written, printed or graphic matter upon any article or any of its containers or wrappers or accompanying such article, for example, a package insert or instructional videotapes or DVDs accompanying or associated with a container of a pharmaceutically active agent.

In certain embodiments, provided herein are compounds of general formula (I) wherein A represents (E)—CH=CHR or —$CH_2CH_2R$, wherein R represents methyl, —$CH_2SH$, —$CH_2$(thioalkyl), —$CH_2$(carboxyl), —$CH_2$(alkoxycarbonyl), carboxyl or alkyoxycarbonyl. In one embodiment, A represents (E)—CH=CHR or —$CH_2CH_2R$, wherein R represents methyl, —$CH_2SH$, —$CH_2$(thioalkyl), —$CH_2$(carboxyl) or —$CH_2$(alkoxycarbonyl). In further embodiments, A represents (E)—CH=CHR. In still further embodiments, A represents —$CH_2CH_2R$. In a preferred embodiment, A represents (E)—CH=CHR.

In one embodiment, R represents methyl.

In certain embodiments, B represents methyl, ethyl, 1-hydroxyethyl, isopropyl or n-propyl. In one embodiment, B represents ethyl, 1-hydroxyethyl, isopropyl or n-propyl. In another embodiment, B represents ethyl.

In one embodiment, $R^1$ represents straight- or branched-chain alkyl containing from one to six carbon atoms, optionally substituted by one or more groups $R^3$ which may be the same or different. In another embodiment, $R^1$ represents straight- or branched-chain alkyl containing from one to four carbon atoms, optionally substituted by one or two groups $R^3$ which may be the same or different. In a further embodiment, $R^1$ represents straight chain alkyl containing from one to three carbon atoms, optionally substituted by one or two groups $R^3$ which may be the same or different. In a still further embodiment, $R^1$ represents alkyl, optionally substituted by one or two groups $R^3$. In yet another embodiment, $R^1$ represents straight chain alkyl containing one to three carbon atoms, optionally substituted by one or two groups $R^3$. In a still further embodiment, $R^1$ represents straight chain alkyl containing one to three carbon atoms, optionally substituted by a group $R^3$.

In certain embodiments, X represents —$S(=O)_n$— or oxygen, wherein n is zero, one or two. In one embodiment, X represents oxygen or sulfur. In a further embodiment, X represents oxygen. In a still further embodiment X represents sulfur.

In one embodiment, $R^2$ represents straight- or branched-chain alkyl containing from one to six carbon atoms, optionally substituted by one or more groups $R^{41}$ which may be the same or different. In another embodiment, $R^2$ represents straight- or branched-chain alkyl containing from one to six carbon atoms, optionally substituted by a group $R^{41}$. In a further embodiment, $R^2$ represents straight chain alkyl containing from one to four carbon atoms substituted by a group $R^{41}$. In a still further embodiment, $R^2$ represents methyl substituted by a group $R^{41}$.

In one embodiment, $R^2$ represents straight- or branched-chain alkyl containing from one to six carbon atoms, optionally substituted by one or more groups $R^{41}$ which may be the same or different. In another embodiment, $R^2$ represents straight- or branched-chain alkenyl containing from three to six carbon atoms optionally substituted by a group $R^{42}$. In another embodiment, $R^2$ represents straight- or branched-chain alkenyl containing from three to six carbon atoms substituted by a group $R^{42}$. In a further embodiment, $R^2$ represents straight- or branched-chain alkenyl containing from three to five carbon atoms optionally substituted by a group $R^{42}$. In a further embodiment, $R^2$ represents straight chain alkenyl containing from three to five carbon atoms substituted by a group $R^{42}$. In a still further embodiment, $R^2$ represents but-2-enyl substituted by a group $R^{42}$. In a still further embodiment, $R^2$ represents trans but-2-enyl substituted by a group $R^{42}$. In a still further embodiment, $R^2$ represents but-2-enyl substituted in the 4-position by a group $R^{42}$ (i.e., —$CH_2CH$=$CHCH_2R^{42}$).

In one embodiment, $R^3$ represents amino, N-alkylamino, N,N-dialkylamino or cycloalkyl. In another embodiment, $R^3$ represents N,N-dimethylaminoethyl, N,N-diethylaminoethyl, N-methyl-N-tert-butylaminoethyl, N-ethyl-N-tert-butylaminoethyl, or cyclobutyl. In a further embodiment, $R^3$ represents N,N-dimethylamino or cyclobutyl.

In one embodiment, $R^{41}$ represents halogen, hydroxyl, alkoxy, carboxyl, alkoxycarbonyl, —$NR^5R^6$, —$NR^7(CH_2)_mNR^5R^6$; or phenyl optionally substituted by from one to five groups which may be the same or different selected from the group consisting of alkyl, haloalkyl, halogen, hydroxyl, alkoxy, amino, N-alkylamino, N,N-dialkylamino, carboxyl and alkoxycarbonyl; or $R^{41}$ is a carbon-linked saturated or unsaturated heterocyclic ring containing from four to six ring atoms, which ring contains one or two heteroatoms which may the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino and N,N-dialkylamino.

In one embodiment, $R^{41}$ represents phenyl optionally substituted by from one to five groups which may be the same or different selected from the group consisting of alkyl, haloalkyl, halogen, hydroxyl, amino, N-alkylamino, N,N-dialkylamino, carboxyl and alkoxycarbonyl. In a further embodiment, $R^{41}$ represents phenyl optionally substituted by a group selected from the group consisting of alkyl, haloalkyl, halogen and alkoxy. In a still further embodiment, $R^{41}$ represents phenyl optionally substituted by a group selected from the group consisting of alkyl and haloalkyl. In a still further embodiment, $R^{41}$ represents —$NR^5R^6$, wherein $R^5$ and $R^6$ which may be the same or different, each represent alkyl.

In one embodiment, $R^{41}$ represents hydroxyl, —$NR^5R^6$, —$OR^8$, carboxyl, alkoxycarbonyl, —C(=O)$NR^5R^6$, formyl or —C(=O)$R^8$. In another embodiment, $R^{41}$ represents hydroxyl, —$NR^5R^6$ or —$OR^8$. In a further embodiment, $R^{41}$ represents hydroxyl, —$NR^5R^6$, —$OR^8$ or phenyl optionally substituted by from one to five groups which may be the same or different selected from the group consisting of alkyl, haloalkyl, halogen, hydroxyl, alkoxy, amino, N-alkylamino, N,N-dialkylamino, carboxyl and alkoxycarbonyl; or cycloalkyl containing from three to six carbon atoms optionally substituted by one or more groups which may be the same or different selected from the group consisting of halogen, hydroxyl, amino, N-monoalkylamino and N,N-dialkylamino.

In one embodiment, $R^{42}$ represents halogen, hydroxyl, amino, N-monoalkylamino or N,N-dialkylamino. In another embodiment, $R^{42}$ represents hydroxyl, —$NR^5R^6$, —$OR^8$, carboxyl, alkoxycarbonyl, —C(=O)$NR^5R^6$, formyl or —C(=O)$R^8$. In a further embodiment, $R^{42}$ represents hydroxyl, —$NR^5R^6$ or —$OR^8$.

In one embodiment, $R^5$ and $R^6$, which may be the same or different, each represent hydrogen; or straight- or branched-chain alkyl containing from one to six carbon atoms; or $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, phenyl and benzyl. In another embodiment, $R^5$ and $R^6$, which may be the same or different, each represent straight- or branched-chain alkyl containing from one to six carbon atoms. In a further embodiment, $R^5$ and $R^6$ each represent methyl.

In one embodiment, $R^8$ represents aryl optionally substituted by one or two groups which may be the same or different selected from the group consisting of alkyl, haloalkyl, halogen, hydroxyl, alkoxy, amino, N-alkylamino and N,N-dialkylamino; or $R^8$ represents aralkyl, wherein the aryl ring is optionally substituted by from one or two groups which may be the same or different selected from the group consisting of halogen, amino, N-alkylamino, N,N-dialkylamino, alkoxy and haloalkyl, wherein the alkyl of aralkyl contains one or two carbon atoms. In a further embodiment, $R^8$ represents benzyl, wherein the phenyl ring is optionally substituted by one or two groups which may be the same or different selected from the group consisting of alkyl, haloalkyl, halogen, hydroxyl and alkoxy. In a further embodiment, $R^8$ represents benzyl, wherein the phenyl ring is optionally substituted by one or two alkoxy groups which may be the same or different.

In certain embodiments, provided herein are compounds of general formula (I) wherein:
A represents (E) —CH=CHR or —$CH_2CH_2R$, wherein R represents methyl, —$CH_2SH$, —$CH_2$(thioalkyl), —$CH_2$(carboxyl) or —$CH_2$(alkoxycarbonyl);
$R^2$ represents:
  straight- or branched-chain alkyl containing from one to six carbon atoms, optionally substituted by one or more groups $R^{41}$ which may be the same or different;
  straight- or branched-chain alkenyl containing from two to six carbon atoms, optionally substituted by one or more groups $R^{42}$ which may be the same or different;
  straight- or branched-chain alkynyl containing from two to six carbon atoms, optionally substituted by one or more groups which may be the same or different selected from the group consisting of halogen, hydroxyl, amino, N-monoalkylamino and N,N-dialkylamino;
  cycloalkyl containing from three to six carbon atoms optionally substituted by one or more groups which may be the same or different selected from the group consisting of halogen, hydroxyl, amino, N-monoalkylamino and N,N-dialkylamino; or
  straight- or branched-chain alkoxycarbonyl containing from two to six carbon atoms;
X represents —$S(=O)_n$— or oxygen, wherein n is zero, one or two;
$R^{41}$ represents halogen, hydroxyl, alkoxy, carboxyl, alkoxycarbonyl, —$NR^5R^6$, —$NR^7(CH_2)_mNR^5R^6$; phenyl optionally substituted by from one to five groups which may be the same or different selected from the group consisting of alkyl, haloalkyl, halogen, hydroxyl, alkoxy, amino, N-alkylamino, N,N-dialkylamino, carboxyl and alkoxycarbonyl; or $R^{41}$ is a carbon-linked saturated or unsaturated heterocyclic ring containing from four to six ring atoms, which ring contains one or two heteroatoms which may the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino and N,N-dialkylamino;
$R^{42}$ represents halogen, hydroxyl, amino, N-monoalkylamino or N,N-dialkylamino;
$R^5$ and $R^6$, which may be the same or different, each represent:

hydrogen;
straight- or branched-chain alkyl containing from one to six carbon atoms;
straight- or branched-chain alkenyl or alkynyl containing from two to four carbon atoms;
cycloalkyl containing from three to six carbon atoms optionally substituted by straight- or branched-chain alkyl containing from one to six carbon atoms;
or $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, phenyl and benzyl;

$R^7$ represents hydrogen, straight- or branched-chain alkyl containing from one to six carbon atoms, cyano or alkylsulfonyl;

and m is an integer from one to four.

Particularly preferred compounds of the invention include the following:
1. [(R)-2-(N,N-Dimethylamino)ethylthio-Sar]$^3$-(N-benzyl)-Val$^5$-cyclosporine A;
2. [(R)-(1-N,N-Dimethylamino-cyclobutylmethylthio)-Sar]$^3$-(N-Benzyl)-Val$^5$-cyclosporine A;
3. [(R)-2-(N,N-Dimethylamino)ethylthio-Sar]$^3$-(4-isopropylbenzyl)-Val$^5$-cyclosporine A;
4. [Methylthio-Sar]$^3$-(N-benzyl)-Val$^5$-cyclosporine A;
5. [n-Propylthio-Sar]$^3$-(N-benzyl)-Val$^5$-cyclosporine A;
6. [Methoxy-Sar]$^3$-(N-benzyl)-Val$^5$-cyclosporine A;
7. [Methoxy-Sar]$^3$-(3-trifluoromethylbenzyl)-Val$^5$-cyclosporine A;
8. [Methoxy-Sar]$^3$-(N-allyl)-Val$^5$-cyclosporine A;
9. [Methoxy-Sar]$^3$-(N-but-2-enyl)-Val$^5$-cyclosporine A;
10. [Methoxy-Sar]$^3$-(N-3-methyl-but-2-enyl)-Val$^5$-cyclosporine A;
11. [Methoxy-Sar]$^3$-N-(trans-4-benzyloxy-but-2-enyl)-Val$^5$-cyclosporine A;
12. [Methylthio-Sar]$^3$-N-[trans-4-(3',4'-dimethoxy)benzyloxy-but-2-enyl]-Val$^5$-cyclosporine A;
13. [Methoxy-Sar]$^3$-N-[trans-4-(3',4'-dimethoxy)benzyloxy-but-2-enyl]-Val$^5$-cyclosporine A;
14. [Methylthio-Sar]$^3$-N-[trans-4-hydroxy-but-2-enyl]-Val$^5$-cyclosporine A;
15. [Methoxy-Sar]$^3$-N-[trans-4-hydroxy-but-2-enyl]-Val$^5$-cyclosporine A;
16. [Methylthio-Sar]$^3$-N-[trans-4-dimethylamino-but-2-enyl]-Val$^5$-cyclosporine A;
17. [Methoxy-Sar]$^3$-N-[trans-4-dimethylamino-but-2-enyl]-Val$^5$-cyclosporine A;
18. [Methoxy-Sar]$^3$-N-[4-hydroxybutyl]-Val$^5$-cyclosporine A;
19. [Methoxy-Sar]$^3$-N-[4-dimethylaminobutyl]-Val$^5$-cyclosporine A;
20. [Methylthio-Sar]$^3$-(N-allyl)-Val$^5$-cyclosporine A; and
21. [Ethylthio-Sar]$^3$-(N-benzyl)-Val$^5$-cyclosporine A.

The numbers 1 to 21 are used to reference and identify these compounds hereafter.

The compounds disclosed herein can be prepared, isolated or obtained by any method apparent to those of skill in the art. Exemplary methods of preparation are described in detail in the examples below.

In certain embodiments, compounds of formula (I) may be prepared by the treatment of a compound of formula (II):

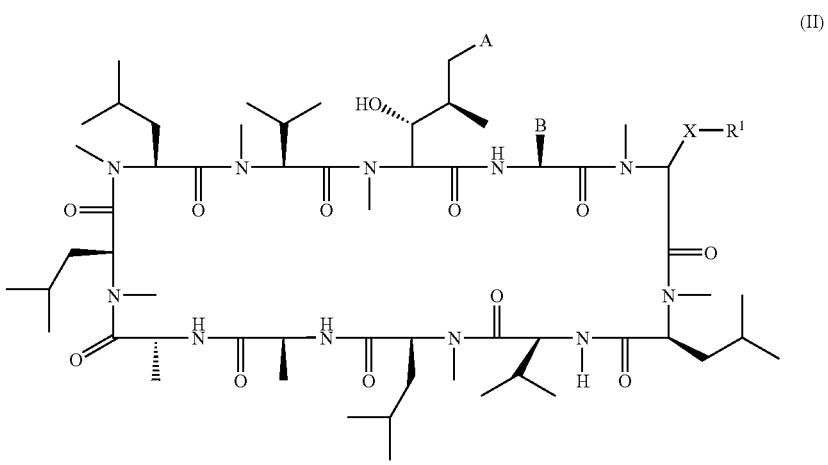

(II)

wherein A, B, X and $R^1$ are as defined above, with a base, followed by reaction of the resulting anionic compound with a compounds of formula $R^2$—Y, wherein $R^2$ is as defined above and Y is a leaving group such as halogen, for example bromide, chloride, iodide; or sulfonate ester such as mesylate, toluenesulfonate or trifluoromethanesulfonate. Preferably the compound of formula (II) is dissolved in an appropriate solvent and cooled to about −70° C. The base is added followed by the electrophile of formula $R^2$—Y and the reaction mixture is allowed to warm to about room temperature. Preferred solvents include tetrahydrofuran, diethyl ether, dimethoxyethane, dioxane, and the like. Suitable bases for the reaction include, but are not limited to, phosphazine bases, sodium hydride, potassium tert-butoxide, lithium diisopropylamide, and the like. Particularly preferred bases include the phosphazine type bases, known in the art as non-nucleophilic bases, such as tert-butyl-4,4,4-tris(dimethylamino)-2,2-bis(tris(dimethylamino)-phosphoranylidenamino)-2$^5$,4$^5$-catenadi(phosphazene) (P$_4$-t-Butyl), and the like. Suitable electrophiles known to react with anionic nitrogen groups include alkyl halides or sulfonates; benzylic halides or sulfonates; heteroarylalkyl halides or sulfonates; allylic halides or sulfonates. Preferred compounds of formula $R^1$—Y include alkyl halides that are further substituted with ether, thioether and ester groups, for example chloromethyl methylether, chloromethyl methylsulfide and tert-butyl bromoacetate.

Compounds of formula (II) are known from the literature or can be prepared by the application or adaptation of known methods.

In certain embodiments, compounds of formula (I) may be prepared by the treatment of a compound of formula (III):

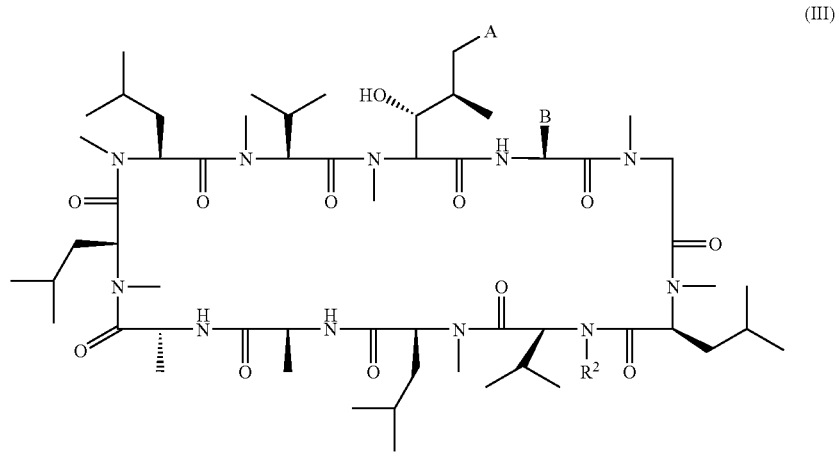

(III)

wherein A, B and $R^2$ are as defined above, with a base in an appropriate solvent to generate a polyanionic species, followed by the reaction of the polyanion thus obtained with a electrophile of formula $R^1$X-L, wherein $R^1$ and X are as defined above and L is a leaving group. Typically the compound of formula (III) is dissolved in an appropriate solvent and cooled to about −70° C. Solvents include tetrahydrofuran, dimethyoxymethane, methyl tert-butylether, dioxane, and the like. Following addition of a base to the mixture, the resulting mixture is generally allowed to react for about 1 hour and is optionally allowed to warm to about −20° C. The reaction mixture is typically cooled to about −70° C. and an appropriate electrophile is added. Preferred bases for this reaction include n-butyl lithium, lithium diisopropylamide, lithium diisopropylamide in combination with lithium chloride and sodium amide. Suitable electrophiles include, but are not limited to activated alkyl and alkenyl halides or sulfonates, disulfides, thiosulfonates, trialkylsilyl halides or sulfonates, and the like.

Polyanions of compounds of formula (III) in which A, B and $R^2$ are as defined above excluding methyl are novel and as such constitute a further feature of the present invention.

Compounds of formula (II) may be prepared by the treatment of a compound of formula (IV):

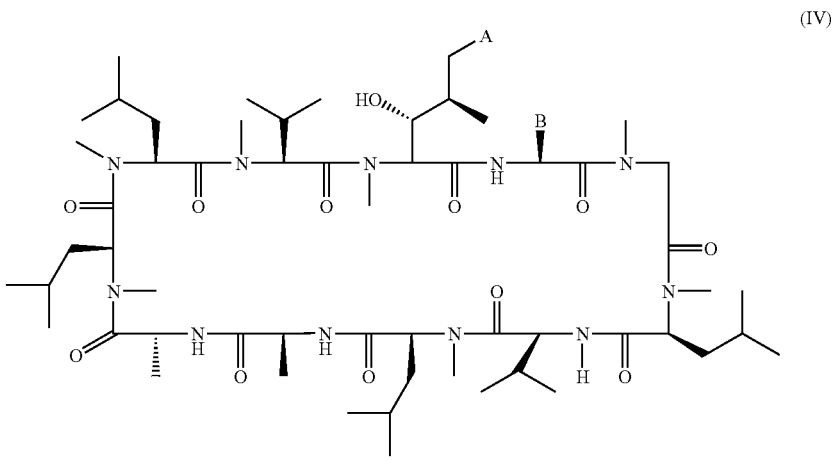

(IV)

wherein A and B are as defined above, with a base followed by reaction of the resulting anionic compound with a compounds of formula $R^1$X—Y, wherein $R^1$ and X are as defined above and Y is a leaving group such as halogen, for example bromide, chloride, iodide; or a sulfonate ester such as mesylate, toluenesulfonate or trifluoromethanesulfonate. Preferably the compound of formula (IV) is dissolved in an appropriate solvent and cooled to about −70° C. The base is added followed by the electrophile of formula $R^1$Y and the reaction mixture is allowed to warm to about room temperature. Preferred solvents include tetrahydrofuran, diethyl ether, dimethoxyethane, dioxane, and the like. Suitable bases for the reaction include, but are not limited to, phosphazine bases, sodium hydride, potassium tert-butoxide, lithium diisopropylamide, and the like. Particularly preferred bases include the phosphazine type bases, known in the art as non-nucleophilic bases, such as tert-butyl-4,4,4-tris(dimethylamino)-2,2-bis(tris(dimethylamino)-phosphoranylidenamino)-$2^5,4^5$-catenadi(phosphazene) ($P_4$-t-Butyl), and the like. Suitable electrophiles known to react with anionic nitrogen groups include alkyl halides or sulfonates; benzylic halides or sulfonates; heteroarylalkyl halides or sulfonates; allylic halides or sulfonates. Preferred compounds of formula $R^1$—Y include alkyl halides that are further substituted with ether, thioether and ester groups, for example chloromethyl methylether, chloromethyl methylsulfide and tert-butyl bromoacetate.

Compounds of formula (IV) above are known or may be prepared by the application and adaptation of known methods.

In certain embodiments, compounds of formula (I) can be prepared by deprotecting a compound of formula (V):

wherein A, B, X, $R^1$ and $R^{50}$ are as defined above, with a base, followed by reaction of the resulting anionic compound with a compound of formula $R^2$—Y, wherein $R^2$ is as defined above and Y. The reaction conditions are generally as described above for the preparation of compounds of formula (I) from compounds of formula (II). Compounds of formula (VI) are known the literature or can be prepared by the application or adaptation of known methods.

Compounds of formula (V) or (VI) may be prepared by treating the corresponding compound of formula (I) or (II) with a reagent known to effect such a protection in an appro-

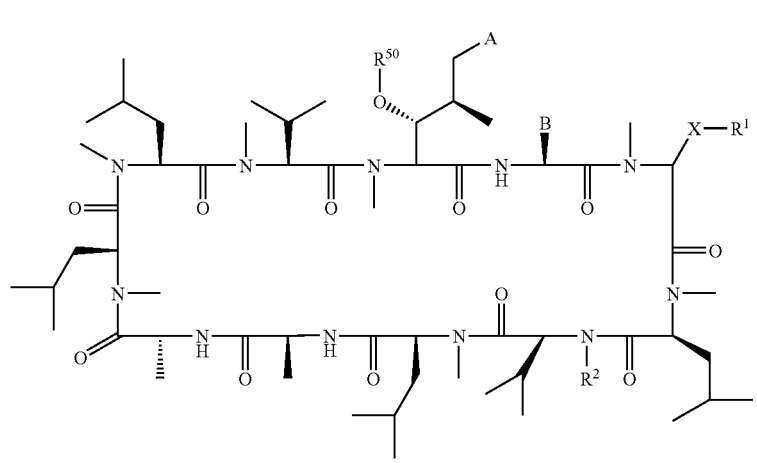

(V)

wherein A, B, X, $R^1$ and $R^2$ are as defined above and $R^{50}$ represents a protecting group. Preferred groups $R^{50}$ include trialkylsilyl such as tert-butyldimethylsiloxy, triethylsilyloxy, tert-butyldiphenylsilyloxy and trimethylsilyloxy. The reaction is generally carried out using a fluoride source (e.g., tetrabutylammonium fluoride, hydrogen fluoride/pyridine, cesium fluoride) in an aprotic solvent (e.g., THF) at a temperature of from about −20 to about 50° C. Compounds of formula (V) are novel and as such form a further feature of the present invention.

Compounds of formula (V) may be prepared by the treatment of a compound of formula (VI):

priate solvent optionally in the presence of a base. Preferably the reagent is a trialkylsilyl derivative, an activated carboxylic acid or an isocyanate, the base is a trialkylamine or an alkaline earth carbonate and the solvent is dichloromethane, dichloroethane, diethyl ether, THF and the like. More preferably the reagent is tert-butyldimethylsilyl trifluoroacetate, the base is triethylamine and the reaction is carried out in dichloroethane.

Compounds of formula (I) may be converted into other compounds of formula (I) by the application and adaptation of known methods, for example as described below.

(VI)

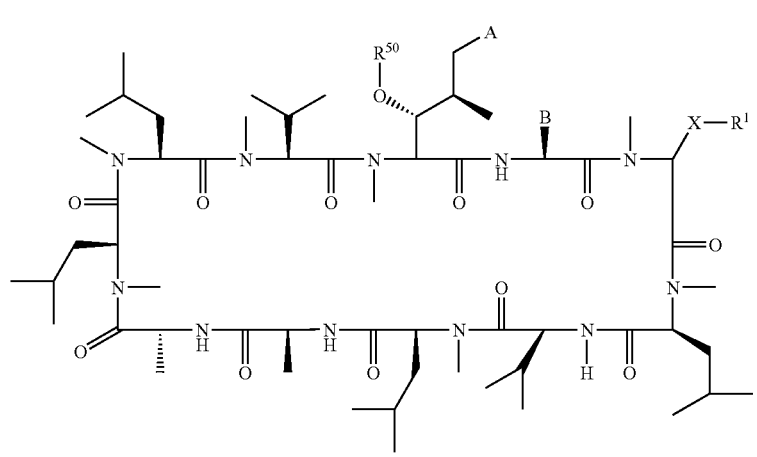

Conversion of compounds of formula (I), (II) or (V) in which X is sulfur and R¹ is an aromatic group, such as phenyl, can be converted into a compound of formula (I), (II) or (V) in which X is oxygen and R¹ is alkyl or aryl by treatment of said sulfur containing derivative with an appropriate alcohol in the presence of a catalysts such as a mercury salt, for example as described in the following reaction scheme:

into the corresponding compound of formula (I), (II) or (V) in which R¹ represents alkyl substituted by carboxyl by selective hydrolysis of the alkoxycarbonyl group, for example, using lithium hydroxide in tetrahydrofuran or sodium hydroxide in ethanol. Compounds of formula (I), (II) or (V) containing carboxyl may be converted into the corresponding compound of formula (I), (II) or (V) in which carboxyl is replaced by

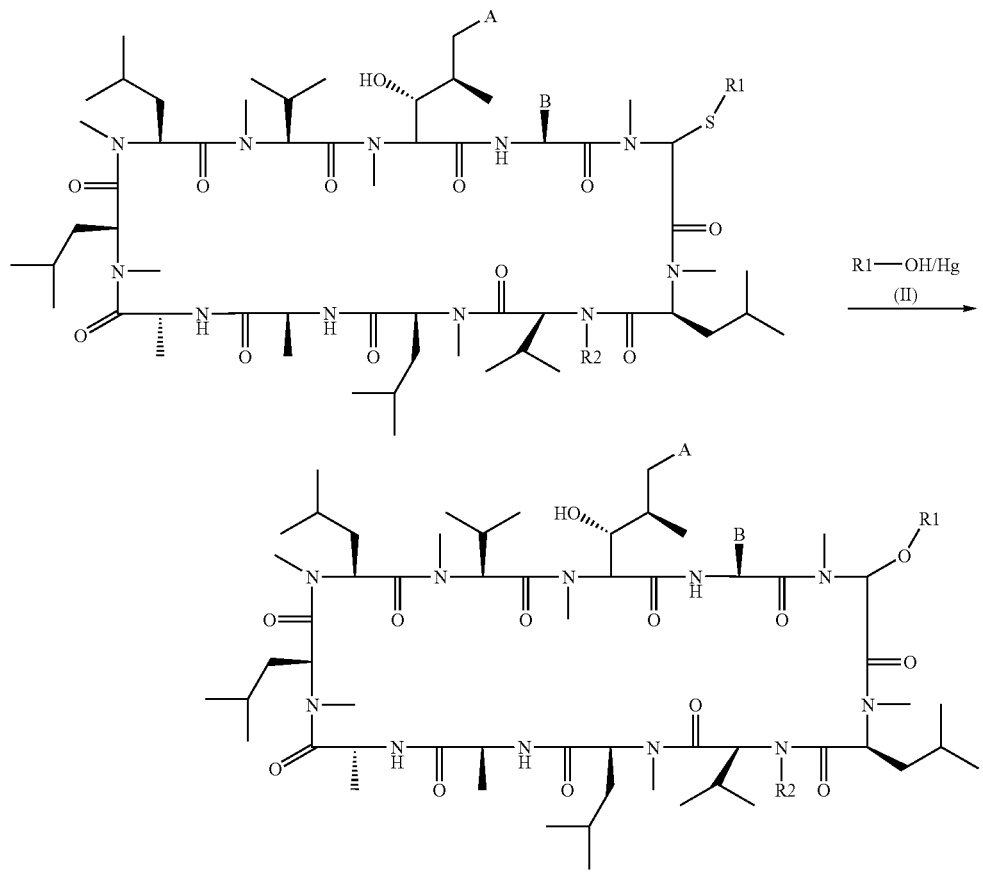

Compounds of formula (I), (II) or (V) in which $R^1$ is alkyl substituted by a phenyl or heterocycle and the phenyl or heterocycle is substituted by halogen (e.g., bromine) can be converted into the corresponding compound of formula (I), (II) or (V) in which $R^1$ is alkyl substituted by a phenyl or heterocycle and the phenyl or heterocycle is substituted by alkyl, aryl or amino using palladium-mediated reactions, for example a Stille reaction, a Suzuki reaction or a Buchwald-Hartwig cross-coupling reaction.

Compounds of formula (I), (II) or (V) in which $R^1$ represents unsubstituted alkenyl can be selectively converted into other compounds of formula (I), (II) or (V) in which $R^1$ is a substituted alkyl using procedures known in the literature. For example selective hydroboration of such compounds can produce the corresponding compound of formula (I), (II) or (V) in which $R^1$ is alkyl substituted by hydroxyl, selective metathesis reactions can lead to new olefin derivatives and selective dihydroxylation can lead to compounds of formula (I), (II) or (V) in which $R^1$ represents alkyl substituted by two hydroxyl.

Compounds of formula (I), (II) or (V) in which $R^1$ represents alkyl substituted by alkoxycarbonyl can be converted amide, alkoxycarbonyl and hydroxyl by the application and adaptation of known methods.

Compounds of formula (I) or (V) in which $R^2$ represents alkyl substituted by alkoxycarbonyl can be converted into the corresponding compound of formula (I) or (V) in which $R^2$ represents alkyl substituted by carboxyl by selective hydrolysis of the alkoxycarbonyl group, for example, using lithium hydroxide in tetrahydrofuran or sodium hydroxide in ethanol. Compounds of formula (I) or (V) containing carboxyl may be converted into the corresponding compound of formula (I) or (V) in which carboxyl is replaced by amide, alkoxycarbonyl and hydroxyl by the application and adaptation of known methods.

Compounds of formula (I) or (V) in which $R^2$ represents alkylene substituted by an ether can be converted into the corresponding compound of formula (I) or (V) in which $R^2$ is hydroxyl by selective deprotection of the ether group. Preferred ethers that can be employed in this procedure include 4-methoxybenzyl, 3,4-dimethoxybenzyl, alkylthiomethyl, tetrahydropyranyl, and the like.

Compounds of formula (I) or (V) in which $R^2$ represents alkenyl substituted by hydroxyl can be converted into the corresponding alkyl derivative by a sequence that involves oxidation of the hydroxyl to give a 1,4-unsaturated carbonyl derivative; followed by selective reduction of the alkenyl group and reduction of the carbonyl to give a hydroxyl compound. Selective reduction of the alkenyl group can be effected by reagents known to cause 1,4 reductions including copper hydrides, lithium/ammonia, sodium hydroxide/iron pentacarbonyl, sodium borohydride/nickel chloride, sodium borohydride/copper sulphate, and the like.

As discussed above, the compounds disclosed herein may be in a neutral form, or in a salt form.

Where a compound of the present invention, e.g., a compound disclosed herein, is substituted with a basic moiety, an acid addition salt can be formed. The acid which can be used to prepare an acid addition salt includes preferably that which produces, when combined with the free base, a pharmaceutically acceptable salt, that is, a salt whose anion is non-toxic to a subject in the pharmaceutical doses of the salt. Pharmaceutically acceptable salts within the scope of the invention are those derived from the following acids: mineral acids such as hydrochloric acid, hydrobromic acid, sulfuric acid, phosphoric acid, sulfamic acid and nitric acid; and organic acids such as acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

The corresponding acid addition salts include hydrohalides, e.g., hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo [2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

According to a further feature of the invention, acid addition salts of the compounds of this invention can be prepared by reaction of the free base with the appropriate acid, by the application or adaptation of known methods. For example, the acid addition salts of the compounds of this invention can be prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention, e.g., compounds disclosed herein, can be regenerated from the salts by the application or adaptation of known methods. For example, parent compounds disclosed herein can be regenerated from their acid addition salts by treatment with an alkali, e.g., aqueous sodium bicarbonate solution or aqueous ammonia solution.

Where a compound of the invention, e.g., a compound of the invention, is substituted with an acid moiety, base addition salts can be formed. Pharmaceutically acceptable salts, including for example alkali and alkaline earth metal salts, within the scope of the invention are those derived from the following bases: sodium hydride, sodium hydroxide, potassium hydroxide, calcium hydroxide, magnesium hydroxide, aluminum hydroxide, lithium hydroxide, zinc hydroxide, barium hydroxide, and organic amines such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylenediamine, chloroprocaine, diethanolamine, procaine, N-benzylphenethylamine, N-methylglucamine piperazine, tris(hydroxymethyl)-aminomethane, tetramethylammonium hydroxide, and the like.

Metal salts of compounds of the present invention, e.g., compounds disclosed herein, can be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention, e.g., compounds disclosed herein, can be obtained by contacting an amine in an aqueous or organic solvent with the free acid form of the compound. Suitable aqueous solvents include water and mixtures of water with alcohols such as methanol or ethanol, ethers such as tetrahydrofuran, nitrites, such as acetonitrile, or ketones such as acetone. Amino acid salts may be similarly prepared.

The base addition salts of the compounds of this invention, e.g., compounds disclosed herein, can be regenerated from the salts by the application or adaptation of known methods. For example, parent compounds disclosed herein can be regenerated from their base addition salts by treatment with an acid, e.g., hydrochloric acid.

Pharmaceutical Compositions and Methods of Administration

The cyclosporine compounds used in the method of the present invention are preferably provided using pharmaceutical compositions containing at least one compound of general formula (I), if appropriate in the salt form, either used alone or in the form of a combination with one or more compatible and pharmaceutically acceptable carriers, such as diluents or adjuvants, or with another therapeutic (e.g., anti-HCV) agent. In clinical practice the cyclosporine compounds of the present invention may be administered by any conventional route, in particular orally, parenterally, rectally or by inhalation (e.g., in the form of aerosols). The cyclosporine compounds of the present invention are preferably administered orally.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In a preferred embodiment, a composition of the invention is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of the invention, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions of the invention can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations, and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions or single unit dosage forms are sterile and in suitable form for administration to a subject, preferably an animal subject, more preferably a mammalian subject, and most preferably a human subject.

A pharmaceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms of the invention will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's *Pharmaceutical Sciences,* 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms of the invention comprise a compound of the invention, or a pharmaceutically acceptable salt, solvate or hydrate thereof lie within the range of from about 0.1 mg to about 1000 mg per day, given as a single once-a-day dose in the morning but preferably as divided doses throughout the day taken with food. Particular dosage forms of the invention have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active cyclosporine.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's *Pharmaceutical Sciences,* 18th ed., Mack Publishing, Easton Pa. (1990).

In preferred embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL PH 10, AVICEL PH 103 AVICEL RC 581, AVICEL PH 105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds disclosed herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

Parenteral Dosage Forms

Although solid, anhydrous oral dosage forms are preferred, the present invention also provides parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are preferably sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical & Mucosal Dosage Forms

Although solid, anhydrous oral dosage forms are preferred, the present invention also provides transdermal, topical, and mucosal dosage forms. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's *Pharmaceutical Sciences,* 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's *Pharmaceutical Sciences,* 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Methods of Treating or Preventing Disease in a Subject

The compounds of the present invention act on enzymes called cyclophilins and inhibit their catalytic activity. Cyclophilins occur in a wide variety of different organisms, including human, yeast, bacteria, protozoa, metazoa, insects, plants, or viruses. In the case of infectious organisms, inhibition of the cyclophilin catalytic activity by compounds of the present invention often results in an inhibitory effect on the organism. Furthermore, in humans the catalytic activity of cyclophilins plays a role in many different disease situations. Inhibition of this catalytic activity is often associated to a therapeutic effect. Therefore, certain compounds of the present invention can be used for the treatment of infections including that by HCV and HIV (described further below) as well as fungal pathogens, protozoan and metazoan parasites. In addition, certain compounds of the present invention can be used to treat neurodegenerative diseases such as Alzheimer's disease, Parkinson's disease, and neuropathies. Another use of the compounds of the present invention is protection against tissue damage associated to ischemia and reperfusion such as paralytic damage after spinal cord or head injuries or cardiac damage after myocardial infarct. Furthermore, the compounds of the present invention induce regenerative processes such as that of hair, liver, gingiva, or nerve tissue damaged or lost due to injury or other underlying pathologies, such as damage of the optical nerve in glaucoma.

Certain compounds of the invention may affect mitochondrial function and the rate of apotosis in muscles cells of patients diagnosed with, for example Faciocaulohumeral (Landouzy-Dejerine), limb-girdle muscular dystrophy including Duchenne and Becker muscular dystrophy, Ullrich congenital muscular dystrophy, and Bethlem myopathy.

Certain compounds of the present invention can be used to treat chronic inflammatory and autoimmune diseases. The regulation of the immune response by the compounds disclosed herein would also find utility in the treatment of autoimmune diseases, such as rheumatoid arthritis, systemic lupus erythematosis, hyperimmunoglobulin E, Hashimoto's thyroiditis, multiple sclerosis, progressive systemic sclerosis, myasthenia gravis, type I diabetes, uveitis, allergic encephalomyelitis, glomerulonephritis. Further uses include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, multiple myeloma, etc.; obstructive airway diseases, which includes conditions such as COPD, asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds disclosed herein. Other treatable conditions would include but are not limited to ischemic bowel diseases; inflammatory bowel diseases, necrotizing enterocolitis, intestinal lesions associated with thermal burns and leukotriene B4-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre-syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (e.g., thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (e.g., paracort and bleomycins), lung cancer and pulmonary emphysema; ocular diseases such as cataracta, siderosis, retinitis, pigmentosa, senile macular degeneration, vitreal scarring and corneal alkali burn; dermatitis. such as erythema multiforme, linear IgA ballous dermatitis and cement dermatitis; and others such as gingivitis, periodontitis, sepsis, pancreatitis, diseases caused by environmental pollution (e.g., air pollution), aging, carcinogenis, metastasis of carcinoma and hypobaropathy; disease caused by histamine or leukotriene-C4 release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds disclosed herein are useful for the treatment and prevention of hepatic disease such as immunogenic diseases (e.g., chronic autoimmune liver diseases such as the group consisting of autoimmune hepatitis, primary biliary cirrhosis and sclerosing cholangitis), partial liver resection, acute liver necrosis, cirrhosis (such as alcoholic cirrhosis) and hepatic failure such as fulminant hepatic failure, late-onset hepatic failure and acute liver failure on chronic liver diseases. Furthermore certain compounds of the invention may also be used for example as a prophylactic treatment of neonates with congenital hepatic fibrosis or of transplant recipients, e.g., organ or tissue transplant recipients, e.g., liver transplant.

Methods of Treating or Preventing HCV Infection in a Subject

Provided herein are methods of using a compound or composition of the invention for the treatment or prevention of a retroviral infection in a subject in need thereof. The methods generally comprise the step of administering to the subject an effective amount of the compound or composition to treat or prevent the retroviral infection. In preferred embodiments, the retroviral infection is HCV infection.

In certain embodiments of the invention, the subject can be any subject infected with, or at risk for infection with, HCV. Infection or risk for infection can be determined according to any technique deemed suitable by the practitioner of skill in the art. Particularly preferred subjects are humans infected with HCV.

The HCV can be any HCV known to those of skill in the art. There are at least six genotypes and at least 50 subtypes of HCV currently known to those of skill in the art. The HCV can be of any genotype or subtype known to those of skill. In certain embodiments, the HCV is of a genotype or subtype not yet characterized. In certain embodiments, the subject is infected with HCV of a single genotype. In certain embodiments, the subject is infected with HCV of multiple subtypes or multiple genotypes.

In certain embodiments, the HCV is genotype 1 and can be of any subtype. For instance, in certain embodiments, the HCV is subtype 1a, 1b or 1c. It is believed that HCV infection of genotype 1 responds poorly to current interferon therapy. Methods of the present invention can be advantageous for therapy of HCV infection with genotype 1.

In certain embodiments, the HCV is other than genotype 1. In certain embodiments, the HCV is genotype 2 and can be of any subtype. For instance, in certain embodiments, the HCV is subtype 2a, 2b or 2c. In certain embodiments, the HCV is genotype 3 and can be of any subtype. For instance, in certain embodiments, the HCV is subtype 3a, 3b or 10a. In certain embodiments, the HCV is genotype 4 and can be of any subtype. For instance, in certain embodiments, the HCV is subtype 4a. In certain embodiments, the HCV is genotype 5 and can be of any subtype. For instance, in certain embodiments, the HCV is subtype 5a. In certain embodiments, the HCV is genotype 6 and can be of any subtype. For instance, in certain embodiments, the HCV is subtype 6a, 6b, 7b, 8b, 9a or 11a. See, e.g., Simmonds, 2004, *J Gen Virol.* 85:3173-88; Simmonds, 2001, *J. Gen. Virol.*, 82, 693-712, the contents of which are incorporated by reference in their entirety.

In certain embodiments of the invention, the subject has never received therapy or prophylaxis for HCV infection. In further embodiments of the invention, the subject has previously received therapy or prophylaxis for HCV infection. For instance, in certain embodiments, the subject has not responded to HCV therapy. Indeed, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for HCV infection but has failed show a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding. Since the compounds of the present invention act by mechanism other than current HCV therapy, it is believed that compounds disclosed herein should be effective in treating such nonresponders.

In certain embodiments, the subject is a subject that discontinued HCV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, the present invention provides methods of treating or preventing HCV infection in subjects where the risk of neuropsychiatric events, such as depression, contraindicates treatment with current HCV therapy. The present invention also provides methods of treating or preventing HCV infection in subjects where a neuropsychiatric event, such as depression, or risk of such indicates discontinuation of treatment with current HCV therapy. The present invention further provides methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects are include bone marrow suppression, neutropenia and thrombocytopenia. Furthermore, ribavirin is toxic to red blood cells and is associated with hemolysis. Accordingly, the present invention also provides methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments the subject has received HCV therapy and discontinued that therapy prior to administration of a method of the invention. In further embodiments, the subject has received therapy and continues to receive that therapy along with administration of a method of the invention. The methods of the invention can be co-administered with other therapy for HCV according to the judgment of one of skill in the art. In advantageous embodiments, the methods or compositions of the invention can be co-administered with a reduced dose of the other therapy for HCV.

In certain embodiments, the present invention provides methods of treating a subject that is refractory to treatment with interferon. For instance, in some embodiments, the subject can be a subject that has failed to respond to treatment with one or more agents selected from the group consisting of interferon, interferon α, pegylated interferon α, interferon plus ribavirin, interferon α plus ribavirin and pegylated interferon α plus ribavirin. In some embodiments, the subject can be a subject that has responded poorly to treatment with one or more agents selected from the group consisting of interferon, interferon α, pegylated interferon α, interferon plus ribavirin, interferon α plus ribavirin and pegylated interferon α plus ribavirin.

In further embodiments, the present invention provides methods of treating HCV infection in subjects that are pregnant or might get pregnant since current therapy is also contraindicated in pregnant women.

In certain embodiments, the methods or compositions of the invention are administered to a subject following liver transplant. Hepatitis C is a leading cause of liver transplantation in the U.S., and many subjects that undergo liver transplantation remain HCV positive following transplantation. The present invention provides methods of treating such recurrent HCV subjects with a compound or composition of the invention. In certain embodiments, the present invention provides methods of treating a subject before, during or following liver transplant to prevent recurrent HCV infection.

Dosage and Unit Dosage Forms

In human therapeutics, the doctor will determine the posology which he considers most appropriate according to a preventive or curative treatment and according to the age, weight, stage of the infection and other factors specific to the subject to be treated. Generally, doses are from about 1 to about 2000 mg per day for an adult, or from about 5 to about 250 mg per day or from about 10 to 50 mg per day for an adult. In certain embodiments, doses are from about 5 to about 400 mg per day, and more preferably 25 to 200 mg per day per adult. Dose rates of from about 50 to about 500 mg per day are also preferred.

In further aspects, the present invention provides methods of treating or preventing HCV infection in a subject by administering, to a subject in need thereof, an effective amount of a compound of the invention, or a pharmaceutically acceptable salt thereof, with a high therapeutic index against HCV. The therapeutic index can be measured according to any method known to those of skill in the art, such as the method described in the examples below. In certain embodiments, the therapeutic index is the ratio of a concentration at which the compound is toxic, to the concentration that is effective against HCV. Toxicity can be measured by any technique known to those of skill including cytotoxicity (e.g., $IC_{50}$ or $IC_{90}$) and lethal dose (e.g., $LD_{50}$ or $LD_{90}$). Likewise, effective concentrations can be measured by any technique known to those of skill including effective concentration (e.g., $EC_{50}$ or $EC_{90}$) and effective dose (e.g., $ED_{50}$ or $ED_{90}$). Preferably, similar measurements are compared in the ratio (e.g., $IC_{50}/EC_{50}$, $IC_{90}/EC_{90}$, $LD_{50}/ED_{50}$ or $LD_{90}/ED_{90}$). In certain embodiments, the therapeutic index can be as high as 2.0, 5.0, 10.0, 15.0, 20.0, 25.0, 50.0, 75.0, 100.0, 125.0, 150.0 or higher.

The amount of the compound or composition of the invention which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions of the invention, the dosage administered to a subject is typically 0.140 mg/kg to 3 mg/kg of the subject's body weight, based on weight of the active compound. Preferably, the dosage administered to a subject is between 0.20 mg/kg and 2.00 mg/kg, or between 0.30 mg/kg and 1.50 mg/kg of the subject's body weight.

In general, the recommended daily dose range of a composition of the invention for the conditions described herein lie within the range of from about 0.1 mg to about 2000 mg per day, given as a single once-a-day dose or as divided doses throughout a day. In one embodiment, the daily dose is administered twice daily in equally divided doses. Specifically, a daily dose range should be from about 10 mg to about 200 mg per day, more specifically, between about 10 mg and about 150 mg per day, or even more specifically between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition of the invention are also encompassed by the above described dosage amounts and dose frequency schedules. Further, when a subject is administered multiple dosages of a composition of the invention, not all of the dosages need be the same. For example, the dosage administered to the subject may be increased to improve the prophylactic or therapeutic effect of the composition or it may be decreased to reduce one or more side effects that a particular subject is experiencing.

In a specific embodiment, the dosage of the composition of the invention or a composition of the invention, based on weight of the active compound, administered to prevent, treat, manage, or ameliorate a disorder, or one or more symptoms thereof in a subject is about 0.1 mg/kg, 1 mg/kg, 2 mg/kg, 3 mg/kg, 4 mg/kg, 5 mg/kg, 6 mg/kg, 10 mg/kg, 15 mg/kg, or 30 mg/kg or more of a subject's body weight. In another embodiment, the dosage of the composition of the invention or a composition of the invention administered to prevent, treat, manage, or ameliorate a disorder, or one or more symptoms thereof in a subject is a unit dose of about 0.1 mg to about 200 mg, about 0.1 mg to about 100 mg, about 0.1 mg to about 50 mg, about 0.1 mg to about 25 mg, about 0.1 mg to about 20 mg, about 0.1 mg to about 15 mg, about 0.1 mg to about 10 mg, about 0.1 mg to about 7.5 mg, about 0.1 mg to about 5 mg, about 0.1 to about 2.5 mg, about 0.25 mg to about 20 mg, about 0.25 to about 15 mg, about 0.25 mg to about 12 mg, about 0.25 to about 10 mg, about 0.25 mg to about 7.5 mg, about 0.25 mg to about 5 mg, about 0.5 mg to about 2.5 mg, about 1 mg to about 20 mg, about 1 mg to about 15 mg, about 1 mg to about 12 mg, about 1 mg to about 10 mg, about 1 mg to about 7.5 mg, about 1 mg to about 5 mg, or about 1 mg to about 2.5 mg.

In certain embodiments, treatment or prevention can be initiated with one or more loading doses of a compound or composition of the invention followed by one or more maintenance doses. In such embodiments, the loading dose can be, for instance, about 60 to about 2000 mg per day, or about 100 to about 200 mg per day for one day to five weeks. The loading dose can be followed by one or more maintenance doses. Each maintenance does can be, independently, about from about 10 mg to about 200 mg per day, more specifically, between about 25 mg and about 150 mg per day, or even more specifically between about 25 and about 80 mg per day. Maintenance doses are preferably administered daily and can be administered as single doses, or as divided doses.

In certain embodiments, a dose of a compound or composition of the invention can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition of the invention is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations of about 1200 to about 8000 ng/mL, or about 2000 to about 4000 ng/mL for one to five days. Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, the present invention provides unit dosages comprising a compound of the invention, or a pharmaceutically acceptable salt thereof, in a form suitable for administration. Such forms are described in detail above. In certain embodiments, the unit dosage comprises 1 to 2000 mg, 5 to 250 mg or 10 to 50 mg active ingredient. In particular embodiments, the unit dosages comprise about 1, 5, 10, 25, 50, 100, 125, 250, 500, 1000 or 2000 mg active ingredient. Such unit dosages can be prepared according to techniques familiar to those of skill in the art.

Combination Therapy

The present invention provides methods of treatment of prevention that comprise the administration of a second agent effective for the treatment or prevention of HCV infection in a subject in need thereof. The second agent can be any agent known to those of skill in the art to be effective for the treatment or prevention of the HCV infection. The second agent can be a second agent presently known to those of skill in the art, or the second agent can be second agent later developed for the treatment or prevention of HCV. In certain embodiments, the second agent is presently approved for the treatment or prevention of HCV.

In certain embodiments, a compound of the invention is administered in combination with one second agent. In further embodiments, a second agent is administered in combination with two second agents. In still further embodiments, a second agent is administered in combination with two or more second agents.

Suitable second agents include small-molecule, orally bioavailable inhibitors of the HCV enzymes, nucleic-acid-based agents that attack viral RNA, agents that can modulate the host immune response. Exemplary second agents include: (i) current approved therapies (peg-interferon plus ribavirin), (ii) HCV-enzyme targeted compounds, (iii) viral-genome-targeted therapies (e.g., RNA interference or RNAi), and (iv) immunomodulatory agents such as ribavirin, interferon (INF) and Toll-receptor agonists.

In certain embodiments, the second agent is a modulator of the NS3-4A protease. The NS3-4A protease is a heterodimeric protease, comprising the amino-terminal domain of the NS3 protein and the small NS4A cofactor. Its activity is essential for the generation of components of the viral RNA replication complex.

One useful NS3-4A protease inhibitor is BILN 2061 (Ciluprevir; Boehringer Ingelheim), a macrocyclic mimic of peptide product inhibitors. Although clinical trials with BILN 2061 were halted (preclinical cardiotoxicity), it was the first NS3 inhibitor to be tested in humans. See Lamarre et al., 2003, *Nature* 426:186-189, the contents of which are hereby incorporated by reference in their entirety.

Another useful NS3-4A protease inhibitor is VX-950 (Vertex/Mitsubishi), a protease-cleavage-product-derived peptidomimetic inhibitor of the NS3-4A protease. It is believed to be stabilized into the enzyme's active site through a ketoamide. See, e.g., Lin et al., 2005, *J. Biol. Chem.* Manuscript M506462200 (epublication); Summa, 2005, *Curr. Opin. Investig. Drugs.* 6:831-7, the contents of which are hereby incorporated by reference in their entireties.

In certain embodiments, the second agent is a modulator of the HCV NS5B The RNA-dependent RNA polymerase (RdRp). Contained within the NS5B protein, RdRp synthesizes RNA using an RNA template. This biochemical activity is not present in mammalian cells.

One useful modulator of RdRp is NM283 (Valopicitabine; Idenix/Novartis). NM283, is an oral prodrug (valine ester) of NM107 (2'-C-methyl-cytidine) in phase II trials for the treatment or prevention of HCV infection. See, e.g., U.S. Patent Application Publication No. 20040077587, the contents of which are hereby incorporated by reference in their entirety.

Other useful modulators of RdRp include 7-deaza nucleoside analogs. For instance, 7-Deaza-2'-C-methyl-adenosine is a potent and selective inhibitor of hepatitis C virus replication with excellent pharmacokinetic properties. Olsen et al., 2004, *Antimicrob. Agents Chemother.* 48:3944-3953, the contents of which are hereby incorporated by reference in their entirety.

In further embodiments, the second agent is a non-nucleoside modulator of NS5B. At least three different classes of non-nucleoside inhibitors (NNI) of NS5B inhibitors are being evaluated in the clinic.

Useful non-nucleoside modulators of NS5B include JTK-003 and JTK-009. JTK-003 has been advanced to phase II. Useful non-nucleoside modulators of NS5B include the 6,5-fused heterocyclic compounds based on a benzimidazole or indole core. See, e.g., Hashimoto et al., WO 2000/147883, the contents of which are hereby incorporated by reference in their entirety.

Further useful polymerase NNIs include R803 (Rigel) and HCV-371, HCV-086 and HCV-796 (ViroPharma/Wyeth). Additional useful NNIs include thiophene derivatives that are reversible allosteric inhibitors of the NS5B polymerase and bind to a site that is close to, but distinct from, the site occupied by benzimidazole-based inhibitors. See, e.g., Biswal, et al., 2005, *J. Biol. Chem.* 280:18202-18210.

Further useful NNIs for the methods of the invention include benzothiadiazines, such as benzo-1,2,4-thiadiazines. Derivatives of benzo-1,2,4-thiadiazine have been shown to be highly selective inhibitors of the HCV RNA polymerase. Dhanak et al., 2002, *J. Biol. Chem.* 277:38322-38327, the contents of which are hereby incorporated by reference in their entirety.

Further useful NNIs for the methods of the invention, and their mechanisms, are described in LaPlante et al., 2004, *Angew Chem. Int. Ed. Engl.* 43:4306-4311; Tomei et al., 2003, *J. Virol.* 77:13225-13231; Di Marco et al., 2005, *J. Biol. Chem.* 280:29765-70; Lu, H., WO 2005/000308; Chan et al., 2004, *Bioorg. Med. Chem. Lett.* 14:797-800; Chan et al., 2004, *Bioorg. Med. Chem. Lett.* 14:793-796; Wang et al., 2003, *J. Biol. Chem.* 278:9489-9495; Love et al., 2003, *J. Virol.* 77:7575-7581; Gu et al., 2003, *J. Biol. Chem.* 278: 16602-16607; Tomei et al., 2004, *J. Virol.* 78:938-946; and Nguyen et al., 2003, *Antimicrob. Agents Chemother.* 47:3525-3530; the contents of each are hereby incorporated by reference in their entireties.

In a further embodiment, the second agent is an agent that is capable of interfering with HCV RNA such as small inhibitory RNA (siRNA) or a short hairpin RNA (shRNA) directed to an HCV polynucleotide. In tissue culture, siRNA and vector-encoded short hairpin RNA shRNA directed against the viral genome, effectively block the replication of HCV replicons. See, e.g., Randall et al., 2003, *Proc. Natl. Acad. Sci. USA* 100:235-240, the contents of which are hereby incorporated by reference in their entirety.

In a further embodiment, the second agent is an agent that modulates the subject's immune response. For instance, in certain embodiments, the second agent can be a presently approved therapy for HCV infection such as an interferon (IFN), a pegylated IFN, an IFN plus ribavirin or a pegylated IFN plus ribavirin. Preferred interferons include IFNα, IFNα2a and IFNα2b, and particularly pegylated IFNα2a (PEGASYS®) or pegylated IFNα2b (PEG-INTRON®).

In a further embodiment, the second agent is a modulator of a Toll-like receptor (TLR). It is believed that TLRs are targets for stimulating innate anti-viral response. Suitable TLRs include, bur are not limited to, TLR3, TLR7, TLR8 and TLR9. It is believed that toll-like receptors sense the presence of invading microorganisms such as bacteria, viruses and parasites. They are expressed by immune cells, including macrophages, monocytes, dendritic cells and B cells. Stimulation or activation of TLRs can initiate acute inflammatory responses by induction of antimicrobial genes and pro-inflammatory cytokines and chemokines.

In certain embodiments, the second agent is a polynucleotide comprising a CpG motif. Synthetic oligonucleotides containing unmethylated CpG motifs are potent agonists of TLR-9. Stimulation of dendritic cells with these oligonucleotides results in the production of tumour necrosis factor-alpha, interleukin-12 and IFN-alpha. TLR-9 ligands are also potent stimulators of B-cell proliferation and antibody secretion. One useful CpG-containing oligonucleotide is CPG-10101 (Actilon; Coley Pharmaceutical Group) which has been evaluated in the clinic.

Another useful modulator of a TLR is ANA975 (Anadys). ANA975 is believed to act through TLR-7, and is known to elicit a powerful anti-viral response via induction and the release of inflammatory cytokines such as IFN-alpha.

In another embodiment, the second agent is Celgosivir. Celgosivir is an alpha-glucosidase I inhibitor and acts through host-directed glycosylation. In preclinical studies, celgosivir has demonstrated strong synergy with IFNα plus ribavirin. See, e.g., Whitby et al., 2004, *Antivir Chem Chemother.* 15(3): 141-51. Celgosivir is currently being evaluated in a Phase II monotherapy study in chronic HCV patients in Canada.

Further immunomodulatory agents, and their mechanisms or targets, are described in Schetter & Vollmer, 2004, *Curr. Opin. Drug Discov. Dev.* 7:204-210; Takeda et al., 2003, *Annu. Rev. Immunol.* 21:335-376; Lee et al., 2003, *Proc. Natl. Acad. Sci. USA* 100:6646-6651; Hosmans et al., 2004, *Hepatology* 40 (Suppl. 1), 282A; and U.S. Pat. No. 6,924,271; the contents of each are hereby incorporated by reference in their entireties.

In certain embodiments, the second agent of the invention can be formulated or packaged with the cyclosporine derivatives of the invention. Of course, the second agent will only be formulated with the cyclosporine derivative of the present invention when, according to the judgment of those of skill in the art, such co-formulation should not interfere with the activity of either agent or the method of administration. In certain embodiment, the cyclosporine derivative of the invention and the second agent are formulated separately. They can be packaged together, or packaged separately, for the convenience of the practitioner of skill in the art.

The dosages of the second agents are to be used in the combination therapies of the invention. In certain embodiments, dosages lower than those which have been or are currently being used to prevent or treat HCV infection are used in the combination therapies of the invention. The recommended dosages of second agents can obtained from the knowledge of those of skill. For those second agents that are approved for clinical use, recommended dosages are described in, for example, Hardman et al., eds., 1996, Goodman & Gilman's *The Pharmacological Basis Of Basis Of Therapeutics* 9th Ed, Mc-Graw-Hill, New York; *Physician's Desk Reference* (PDR) 57th Ed., 2003, Medical Economics Co., Inc., Montvale, N.J., which are each incorporated herein by reference in its entirety.

In various embodiments, the therapies (e.g., the cyclosporine derivative of the invention and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patent visit.

In certain embodiments, the cyclosporine derivative of the invention and the second agent are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a cyclosporine derivative of the invention and a second agent are administered to a patient, preferably a mammal, more preferably a human, in a sequence and within a time interval such that the cyclosporine derivative can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the cyclosporine derivative and the second active agent exert their effect at times which overlap. Each second active agent can be administered separately, in any appropriate form and by any suitable route. In other embodiments, the cyclosporine derivative is administered before, concurrently or after administration of the second active agent.

In various embodiments, the cyclosporine derivative and the second agent are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other embodiments, the cyclosporine derivative and the second agent are administered concurrently.

In other embodiments, the cyclosporine derivative and the second agent are administered at about 2 to 4 days apart, at about 4 to 6 days apart, at about 1 week part, at about 1 to 2 weeks apart, or more than 2 weeks apart.

In certain embodiments, the cyclosporine derivative and the second agent are cyclically administered to a patient. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improve the efficacy of the treatment.

In certain embodiments, the cyclosporine derivative and the second active agent are administered in a cycle of less than about 3 weeks, about once every two weeks, about once every 10 days or about once every week. One cycle can comprise the administration of a cyclosporine derivative and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the cyclosporine derivative can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or, more preferably, synergistically with the cyclosporine derivative. In one embodiment, a cyclosporine derivative is administered concurrently with one or more second agents in the same pharmaceutical composition. In another embodiment, a cyclosporine derivative is administered concurrently with one or more second agents in separate pharmaceutical compositions. In still another embodiment, a cyclosporine derivative is administered prior to or subsequent to administration of a second agent. The invention contemplates administration of a cyclosporine derivative and a second agent by the same or different routes of administration, e.g., oral and parenteral. In certain embodiments, when a cyclosporine derivative is administered concurrently with a second agent that potentially produces adverse side effects including, but not limited to, toxicity, the second active agent can advantageously be administered at a dose that falls below the threshold that the adverse side effect is elicited.

Kits

The invention also provides kits for use in methods of treatment or prophylaxis of HCV infection. The kits can include a pharmaceutical compound or composition of the invention and instructions providing information to a health care provider regarding usage for treating or preventing a bacterial infection. Instructions may be provided in printed form or in the form of an electronic medium such as a floppy disc, CD, or DVD, or in the form of a website address where such instructions may be obtained. A unit dose of a compound or composition of the invention can include a dosage such that when administered to a subject, a therapeutically or prophylactically effective plasma level of the compound or composition can be maintained in the subject for at least 1 day. In some embodiments, a compound or composition of the invention can be included as a sterile aqueous pharmaceutical composition or dry powder (e.g. lyophilized) composition. In one embodiment, the compound is according to formula (I).

In some embodiments, suitable packaging is provided. As used herein, "packaging" refers to a solid matrix or material customarily used in a system and capable of holding within fixed limits a compound or composition of the invention suitable for administration to a subject. Such materials include glass and plastic (e.g. polyethylene, polypropylene, and polycarbonate) bottles, vials, paper, plastic, and plastic-foil laminated envelopes, and the like. If e-beam sterilization techniques are employed, the packaging should have sufficiently low density to permit sterilization of the contents.

Kits of the invention may also comprise, in addition to the compound or composition of the invention, second agents or compositions comprising second agents for use with compound or composition as described in the methods above.

The following Examples illustrate the synthesis of representative cyclosporine compounds used in the present invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

Example 1

Diisopropylamine (300 mg) was dissolved in anhydrous tetrahydrofuran. This solution was cooled to −25° C. under nitrogen. n-Butyl lithium (2.5M/hexanes, 1.2 mL) was added and then the mixture was stirred for 30 minutes at −25° C. N-Benzyl-Val$^5$-cyclosporine A (320 mg) made, for example, according to Reference Example 1, was dissolved in anhydrous tetrahydrofuran, and was added to the solution. The mixture was kept at this temperature for 90 minutes and then toluene-4-thiosulfonic acid S-(2-dimethylaminoethyl)ester (390 mg) in anhydrous tetrahydrofuran was added to the solution. The solution was stirred at −25° C. for 2 hours and then left to warm to room temperature overnight. The reaction was quenched by adding a saturated solution of ammonium chloride and then extracted twice with ethyl acetate. The combined organic layers were dried over sodium sulfate and concentrated. Some of the crude material was purified using HPLC to give [(R)-2-(N,N-dimethylamino)ethylthio-Sar]$^3$-(N-Benzyl)-Val$^5$-cyclosporine A (Compound 1); $^1$H NMR (400 MHz, DMSO-d$_6$) δ ppm 1.70 (s, 6H) 2.39 (s, 3H) 2.40 (s, 3H) 2.41 (s, 3H) 2.47 (s, 3H) 2.55 (s, 3H) 2.66 (s, 3H) 2.77 (s, 3H) 5.95 (s, 1H) 6.13 (d, 1H) 6.61 (d, 2H) 6.78-6.95 (m, 3H) 7.76 (d, 1H) 8.07 (d, 1H); mass spectra: 708.5, (M+Na)/2.

By proceeding in a similar manner the following compounds were prepared:

[(R)-(1-N,N-Dimethylamino-cyclobutylmethylthio)-Sar]$^3$-(N-Benzyl)-Val$^5$-cyclosporine A (Compound 2), $^1$H NMR (400 MHz, DMSO-d$_6$) δ ppm 1.54 (s, 3H) 1.55 (s, 3H) 2.70 (s, 3H) 2.71 (s, 6H) 2.78 (s, 3H) 2.86 (s, 3H) 2.97 (s, 3H) 3.10 (s, 3H) 6.25 (s, 1H) 6.46 (d, 1H) 6.92 (d, 2H) 7.10-7.23 (m, 3H) 8.08 (d, 1H) 8.36 (d, 1H); mass spectra: 728.5, (M+Na)/2.

[(R)-2-(N,N-Dimethylamino)ethylthio-Sar]$^3$-(4-isopropylbenzyl)-Val$^5$-cyclosporine A (Compound 3), $^1$H NMR (400 MHz, DMSO-d$_6$) δ ppm 0.33 (d, 3H) 0.41 (d, 3H) 1.85 (s, 6H) 2.53 (s, 3H) 2.54 (s, 3H) 2.55 (s, 3H) 2.67 (s, 3H) 2.71 (s, 3H) 2.81 (s, 3H) 2.90 (s, 3H) 6.14 (s, 1H) 6.35 (d, 1H) 6.68 (d, 2H) 6.88 (d, 2H) 7.90 (d, 1H) 8.18 (d, 1H); mass spectra: 729.5, (M+Na)/2.

Example 2

[(R)-Methylthio-Sar]$^3$-cyclosporine A (150 mg) made, for example, according to Reference Example 2, and benzyl bromide (85.5 mg) were charged in an oven dried flask. Anhydrous tetrahydrofuran was added to the reaction vessel. This solution was cooled to −78° C. under a stream of nitrogen. Phosphazene base P$_4$-tBu (CAS: [111324-04-0], 1M/hexanes, 0.5 mL) was slowly added. The reaction mixture was left to warm to −30° C. and then quenched with citric acid (1N). The reaction was further diluted with ethyl acetate and then extracted twice with ethyl acetate. The combined organic layers were washed with saturated solutions of sodium bicarbonate and then brine. After drying over sodium sulfate, it was concentrated and purified by flash chromatography (40 g ISCO silica cartridge, gradient ethyl acetate/heptanes) to afford [methylthio-Sar]$^3$-(N-benzyl)-Val$^5$-cyclosporine A (Compound 4) as a white solid, $^1$H NMR (400 MHz, DMSO-d$_6$) δ ppm 1.66 (s, 3H) 2.45 (s, 3H) 2.47 (s, 3H) 2.48 (s, 3H) 2.58 (s, 3H) 2.58 (s, 3H) 2.75 (s, 3H) 2.79 (s, 3H) 5.98 (s, 1H) 6.37 (d, 1H) 6.70 (d, 2H) 6.86-7.00 (m, 3H) 7.84 (d, 1H) 8.08 (d, 1H); mass spectra: 691.5 (M+2Na)/2.

By proceeding in a similar manner the following compounds were prepared:

[n-Propylthio-Sar]$^3$-(N-Benzyl)-Val$^5$-cyclosporine A (Compound 5) $^1$H NMR (400 MHz, DMSO-d$_6$) δ ppm 2.41 (s, 3H) 2.42 (s, 3H) 2.43 (s, 3H) 2.49 (s, 3H) 2.55 (s, 3H) 2.68 (s, 3H) 2.77 (s, 3H) 5.91 (s, 1H) 6.10 (s, 1H) 6.16 (d, 1H) 6.63 (d, 2H) 6.82-6.95 (m, 3H) 7.79 (d, 1H) 8.07 (d, 1H); mass spectra: 705.5, (M+2Na)/2.

[Methoxy-Sar]$^3$-(N-Benzyl)-Val$^5$-cyclosporine A (Compound 6) $^1$H NMR (400 MHz, DMSO-d$_6$) δ ppm 2.80 (s, 3H) 2.81 (s, 3H) 2.84 (s, 3H) 2.86 (s, 6H) 2.94 (s, 3H) 3.06 (s, 3H) 3.28 (s, 3H) 5.93 (s, 1H) 6.52 (d, 1H) 7.02 (d, 2H) 7.18-7.36 (m, 3H) 8.12 (d, 1H) 8.49 (d, 1H); mass spectra: 683.5, (M+2Na)/2.

[Methoxy-Sar]$^3$-(3-trifluoromethylbenzyl)-Val$^5$-cyclosporine A (Compound 7) $^1$H NMR (400 MHz, DMSO-d$_6$) δ ppm 2.80 (s, 3H) 2.81 (s, 3H) 2.82 (s, 3H) 2.85 (s, 3H) 2.88 (s, 3H) 2.93 (s, 3H) 3.08 (s, 3H) 3.28 (s, 3H) 5.95 (s, 1H) 6.47 (d, 1H) 7.30 (d, 1H) 7.41 (s, 1H) 7.58 (t, 1H) 7.63-7.67 (m, 1H) 8.13 (d, 1H) 8.49 (d, 1H); mass spectra: 717.5, (M+2Na)/2.

[Methoxy-Sar]$^3$-(N-allyl)-Val$^5$-cyclosporine A (Compound 8) $^1$H NMR (400 MHz, DMSO-d$_6$) δ ppm 2.79 (s, 3H) 2.81 (s, 3H) 2.82 (s, 3H) 2.85 (s, 3H) 2.89 (s, 3H) 2.91 (s, 3H) 3.02 (s, 3H) 3.32 (s, 3H) 5.90 (s, 1H) 6.52 (d, 1H) 8.09 (d, 1H) 8.58 (d, 1H); mass spectra: 1273.0, (M+H).

[Methoxy-Sar]$^3$-(N-but-2-enyl)-Val$^5$-cyclosporine A (Compound 9) $^1$H NMR (400 MHz, DMSO-d$_6$) δ ppm 2.79 (s, 3H) 2.80 (s, 3H) 2.84 (s, 6H) 2.88 (s, 3H) 2.90 (s, 3H) 3.02 (s, 3H) 3.31 (s, 3H) 5.92 (s, 1H) 6.53 (d, 1H) 8.09 (d, 1H) 8.58 (d, 1H); mass spectra: 1287.0, (M+H).

[Methoxy-Sar]$^3$-(N-3-methyl-but-2-enyl)-Val$^5$-cyclosporine A (Compound 10) $^1$H NMR (400 MHz, DMSO-d$_6$) δ ppm 2.77 (s, 3H) 2.79 (s, 3H) 2.80 (s, 3H) 2.85 (s, 3H) 2.88 (s, 3H) 2.91 (s, 3H) 3.02 (s, 3H) 3.24 (s, 3H) 6.00 (s, 1H) 6.85 (d, 1H) 8.12 (d, 1H) 8.41 (d, 1H); mass spectra: 1301.0, (M+H).

[Methoxy-Sar]$^3$-N-(trans-4-benzyloxy-but-2-enyl)-Val$^5$-cyclosporine A (Compound 11) $^1$H NMR (400 MHz, DMSO-d$_6$) δ ppm 2.79 (s, 3H) 2.80 (s, 3H) 2.84 (s, 6H) 2.90 (s, 3H) 2.94 (s, 3H) 3.02 (s, 3H) 3.31 (s, 3H) 5.85-5.89 (m, 1H) 5.92 (s, 1H) 6.50 (d, 1H) 7.22-7.34 (m, 5H) 8.08 (d, 1H) 8.59 (d, 1H); mass spectra: 1393.0, (M+H).

[Methylthio-Sar]$^3$-N-[trans-4-(3',4'-dimethoxy)benzyloxy-but-2-enyl]-Val$^5$-cyclosporine A (Compound 12) $^1$H NMR (400 MHz, DMSO-d$_6$) δ ppm 2.06 (s, 3H) 2.78 (s, 3H) 2.80 (s, 3H) 2.84 (s, 3H) 2.86 (s, 3H) 2.93 (s, 3H) 2.96 (s, 3H) 3.24 (s, 3H) 3.70 (s, 3H) 3.71 (s 3H) 5.83-5.87 (m, 1H) 6.20 (s, 1H) 6.53 (d, 1H) 6.83-6.91 (m, 3H) 8.13 (d, 1H) 8.56 (d, 1H); mass spectra: 1469.0, (M+H).

[Methoxy-Sar]$^3$-N-[trans-4-(3',4'-dimethoxy)benzyloxy-but-2-enyl]-Val$^5$-cyclosporine A (Compound 13) $^1$H NMR (400 MHz, DMSO-d$_6$) δ ppm 2.78 (s, 3H) 2.80 (s, 3H) 2.84 (s, 3H) 2.84 (s, 3H) 2.90 (s, 3H) 2.94 (s, 3H) 3.03 (s, 3H) 3.31 (s, 3H) 3.70 (s, 3H) 3.71 (s 3H) 5.85-5.92 (m, 1H) 5.92 (s, 1H) 6.48 (d, 1H) 6.83-6.90 (m, 3H) 8.08 (d, 1H) 8.60 (d, 1H); mass spectra: 1453.0, (M+H).

[Methylthio-Sar]$^3$-(N-allyl)-Val$^5$-cyclosporine A (Compound 20) $^1$H NMR (400 MHz, DMSO-d$_6$) δ ppm 2.80 (s, 3H), 2.81 (s, 3H), 2.81 (s, 3H), 2.87 (s, 3H), 2.94 (s, 3H), 3.07 (s, 3H), 3.16 (s, 3H), 6.32 (s, 1H), 6.54 (d, J=7.5 Hz, 1H), 7.02 (d, J=7.3 Hz, 2H), 7.20-7.34 (m, 3H), 8.18 (d, J=7.2 Hz, 1H), 8.46 (d, J=7.0 Hz, 1H)

[Ethylthio-Sar]$^3$-(N-benzyl)-Val$^5$-cyclosporine A. (Compound 21) $^1$H NMR (400 MHz, DMSO-d$_6$) δ ppm 2.07 (s, 3H), 2.79 (s, 3H), 2.81 (s, 3H), 2.82 (s, 3H), 2.86 (s, 3H), 2.94 (s, 3H), 2.94 (s, 3H), 3.24 (s, 3H), 6.16 (s, 1H), 6.55 (d, J=8.3 Hz, 1H), 8.13 (d, J=7.0 Hz, 1H) 8.56 (d, J=6.6 Hz, 1H).

Example 3

To a solution of [methylthio-Sar]$^3$-N-[trans-4-(3',4'-dimethoxy)benzyloxy-but-2-enyl]-Val$^5$-cyclosporine A (Compound 12) (0.25 g) in a solvent mixture of dichloromethane and water was added 2,3-dichloro-5,6-dicyano-p-benzoquinone (DDQ) (40 mg) and the resulting mixture was stirred at room temperature for 2 hours. It was diluted with dichloromethane, washed with saturated sodium bicarbonate solution, saturated sodium chloride solution, and then concentrated under reduced pressure. The crude product was purified using flash silica gel column chromatography, eluting with a gradient of 0 to 100% ethyl acetate in heptane to yield [methylthio-Sar]$^3$-N-[trans-4-hydroxy-but-2-enyl]-Val$^5$-cyclosporine A (Compound 14) as a white solid; $^1$H NMR (400 MHz, DMSO-d$_6$) δ ppm 2.04 (s, 3H) 2.79 (s, 3H) 2.80 (s, 3H) 2.83 (s, 3H) 2.84 (s, 3H) 2.93 (s, 3H) 2.96 (s, 3H) 3.21 (s, 3H) 5.78-5.82 (m, 1H) 6.25 (s, 1H) 6.61 (d, 1H) 8.14 (d, 1H) 8.51 (d, 1H); mass spectra: 1318.9, (M+H).

By proceeding in a similar manner [methoxy-Sar]$^3$-N-[trans-4-hydroxy-but-2-enyl]-Val$^5$-cyclosporine A (Compound 15) was prepared starting from [methoxy-Sar]$^3$-N-[trans-4-(3',4'-dimethoxy)benzyloxy-but-2-enyl]-Val$^5$-cyclosporine A (Compound 13), $^1$H NMR (400 MHz, DMSO-d$_6$) δ ppm 2.79 (s, 3H) 2.80 (s, 3H) 2.84 (s, 3H) 2.85 (s, 3H) 2.87 (s, 3H) 2.92 (s, 3H) 3.01 (s, 3H) 3.30 (s, 3H) 5.77-5.82 (m, 1H) 5.93 (s, 1H) 6.55 (d, 1H) 8.09 (d, 1H) 8.56 (d, 1H); mass spectra: 1302.9, (M+H).

Example 4

To a solution of [methylthio-Sar]$^3$-N-[trans-4-hydroxy-but-2-enyl]-Val$^5$-cyclosporine A (Compound 14) (200 mg, 0.16 mmol) in dry dichloromethane cooled at 0° C. in an ice bath under nitrogen, were added triethylamine (0.06 mL, 2.4 eq) and methanesulfonyl chloride (0.03 mL, 2.4 eq). The resulting mixture was stirred at room temperature for 2 hours. It was diluted with dichloromethane, washed successively with water and brine. The organic layer was dried over anhydrous magnesium sulfate and concentrated under reduced pressure. The residue was dissolved in THF and to this solution were added triethylamine (0.06 mL, 4.0 eq) and dimethylamine (0.29 mL, 5.0 eq, 2.0 M solution in THF). The resulting mixture was stirred at room temperature overnight under nitrogen. The solvent was removed under reduced pressure and the residue was purified using preparative HPLC to yield [methylthio-Sar]$^3$-N-[trans-4-dimethylamino-but-2-enyl]-Val$^5$-cyclosporine A (Compound 16) as a white solid after lyphilization; $^1$H NMR (400 MHz, DMSO-d$_6$) δ ppm 2.08 (s, 3H) 2.11 (s, 6H) 2.77 (s, 3H) 2.81 (s, 3H) 2.83 (s, 3H) 2.88 (s, 3H) 2.92 (s, 3H) 2.93 (s, 3H) 3.28 (s, 3H) 5.75-5.83 (m, 1H) 6.13 (s, 1H) 6.44 (d, 1H) 8.09 (d, 1H) 8.61 (d, 1H); mass spectra: 1345.9 (M+H).

By proceeding in a similar manner [methoxy-Sar]$^3$-N-[trans-4-dimethylamino-but-2-enyl]-Val$^5$-cyclosporine A (Compound 17) was prepared starting from [methoxy-Sar]$^3$-N-[trans-4-hydroxy-but-2-enyl]-Val$^5$-cyclosporine A (Compound 15), $^1$H NMR (400 MHz, DMSO-d$_6$) δ ppm 2.11 (s, 6H) 2.77 (s, 3H) 2.81 (s, 3H) 2.82 (s, 3H) 2.84 (s, 3H) 2.90 (s, 3H) 3.05 (s, 3H) 3.33 (s, 3H) 5.80-5.87 (m, 1H) 5.90 (s, 1H) 6.42 (d, 1H) 8.04 (d, 1H) 8.63 (d, 1H); mass spectra: 1329.9, (M+H).

Example 5

To a solution of [3'-tert-butyldimethylsiloxy-N-methyl-Bmt]$^1$-[methoxy-Sar]$^3$-N-[4-hydroxybutyl]-Val$^5$-cyclosporine A (90 mg) in THF was added tetrabutylammonium fluoride (0.1 mL, 1.5 eq, 1.0 M solution in THF) and the resulting mixture was stirred at room temperature for 12 hours. It was diluted with ethyl acetate, washed successively with water and brine and dried over anhydrous sodium sulfate. The solvent was removed under reduced pressure and the residue was purified using flash silica gel column chromatography, eluting with a gradient of 0 to 100% ethyl acetate in heptane to yield [methoxy-Sar]$^3$-N-[4-hydroxybutyl]-Val$^5$-cyclosporine A (Compound 18) as a white solid; $^1$H NMR (400 MHz, DMSO-d$_6$) δ ppm 2.80 (s, 6H) 2.82 (s, 3H) 2.84 (s, 3H) 2.86 (s, 3H) 2.96 (s, 3H) 2.97 (s, 3H) 3.28 (s, 3H) 5.96 (s, 1H), 6.72 (d, 1H) 8.10 (d, 1H) 8.49 (d, 1H); mass spectra: 653.1 (M+2H)/2.

Example 6

To a solution of [3'-tert-butyldimethylsiloxy-N-methyl-Bmt]$^1$-[methoxy-Sar]$^3$-N-[4-dimethylaminobutyl]-Val$^5$-cyclosporine A (90 mg) in THF was added tetrabutylammonium fluoride (0.09 mL, 1.5 eq, 1.0 M solution in THF) and the resulting mixture was stirred at room temperature for 12 hours. It was diluted with ethyl acetate, washed successively with water and brine (10 mL) and dried over anhydrous sodium sulfate. The solvent was removed under reduced pressure and the residue was purified using flash silica gel column chromatography, eluting with a gradient of 0 to 70% of solvent B (B=DCM/MeOH/NH$_4$OH (90:9:1, v/v/v) in solvent A (A=DCM) to yield [methoxy-Sar]$^3$-N-[4-dimethylaminobutyl]-Val$^5$-cyclosporine A (Compound 19) as a white solid; $^1$H NMR (400 MHz, DMSO-d$_6$) δ ppm 2.11 (s, 6H) 2.79 (s, 6H) 2.80 (s, 3H) 2.86 (s, 3H) 2.90 (s, 3H) 2.97 (s, 3H) 3.01 (s, 3H) 3.29 (s, 3H) 5.94 (s, 1H), 6.57 (d, 1H) 8.06 (d, 1H) 8.57 (d, 1H); mass spectra: 666.6 (M+2H)/2.

Reference Example 1

Cyclosporine A (3.0 g) and benzyl bromide (1.8 g) were charged in an oven dried flask. Anhydrous tetrahydrofuran was added in the reaction vessel. The solution was cooled to −78° C. under a stream of nitrogen. Phosphazene base P$_4$-tBu (CAS: [111324-04-0], 1M/hexanes, 10.5 mL) was slowly added. The reaction mixture was left to warm to −30° C. then quenched with citric acid (1N), diluted with ethyl acetate then extracted twice with ethyl acetate. The combined organic layers were washed with a saturated solution of sodium bicarbonate and brine. After drying over sodium sulfate, it was concentrated and purified on a Combiflash® system (120 g ISCO silica cartridge, gradient ethyl acetate/heptanes) to afford N-benzyl-Val$^5$-cyclosporine A as a white solid; $^1$H NMR (400 MHz, DMSO-d$_6$) δ ppm 2.77 (s, 3H) 2.78 (s, 3H) 2.79 (s, 3H) 2.81 (s, 3H) 2.89 (s, 3H) 3.01 (s, 3H) 3.03 (s, 3H) 6.29 (d, 1H) 6.98 (d, 2H) 7.17-7.34 (m, 3H) 7.92 (d, 1H) 8.55 (d, 1H); mass spectra: 669.5 (M+2Na)/2.

By proceeding in a similar manner the following compounds of formula (III) in which A is (E)—CH=CHCH$_3$ and B is ethyl were prepared:

| R$^2$ | $^1$H NMR (400 MHz, DMSO-d$_6$, δ ppm) | Mass Spec. (M + 2Na)/2 |
|---|---|---|
| 4-isopropyl-benzyl | 2.50 (s, 3H) 2.53 (s, 3H) 2.55 (s, 3H) 2.61 (s, 3H) 2.63 (s, 3H) 2.76 (s, 3H) 2.78 (s, 3H) 6.01 (d, 1H) 6.65 (d, 2H) 6.89 (d, 2H) 7.68 (d, 1H) 8.30 (d, 1H) | 689.5 |
| 3-trifluoromethylbenzyl | 2.50 (s, 3H) 2.51 (s, 3H) 2.52 (s, 3H) 2.53 (s, 3H) 2.60 (s, 3H) 2.76 (s, 3H) 2.77 (s, 3H) 5.90 (d, 1H) 6.96 (d, 1H) 7.05 (s, 1H) 7.25-7.40 (m, 2H) 7.64 (d, 1H) 8.29 (d, 1H) | 702.5 |

Reference Example 2

A solution of cyclosporine A (1.2 g) in dry t-butyl methyl ether (TBME) was added to a suspension of sodium amide (1.0 g) in liquid ammonia (30 mL) at −33° C. under inert atmosphere. The resulting mixture was stirred at −33° C. for 90 minutes under an inert atmosphere. Dimethyl disulfide (1.9 g) was then added, and the reaction mixture was stirred for an additional 2 hours at −33° C. under an inert atmosphere. Solid ammonium chloride (1.4 g) was added and stirring was continued at −33° C. for 10 minutes. After warming to room temperature, the reaction mixture was diluted with TBME and water, mixed thoroughly, and the layers separated. The organic layer was washed with brine and then concentrated. The residue was purified by chromatography using a silica gel column eluting first with a mixture of ethyl acetate and heptane to yield [2'-methylthio-Sar]$^3$-cyclosporine A.

By proceeding in a similar manner, [2'-propylthio-Sar]$^3$-cyclosporine A was also prepared.

Reference Example 3

To a solution of trans-1,4-dibromobut-2-ene (20.0 g, 93.5 mmol), benzyl alcohol (10.6 mL, 102.9 mmol), and tetrabutylammonium hydrogensulfate (3.17 g, 9.35 mmol) in dichloromethane (80 mL) were added sodium hydroxide (33.7 g, 841 mmol) in water and the resulting mixture was stirred at room temperature for 24 hours. It was diluted with water and extracted with diethyl ether. The combined organic extracts were dried over anhydrous sodium sulfate and concentrated under reduced pressure. The crude product was purified using flash column chromatography to yield 10.8 g of trans-4-benzyloxy-1-bromo-2-butene; $^1$H NMR (400 MHz, CDCl$_3$) δ ppm 3.98 (d, 2H, J=7.3 Hz) 4.04 (d, 2H, J=4.4 Hz) 4.54 (s, 2H) 5.82-6.08 (m, 2H) 7.25-7.45 (m, 5H).

By proceeding in a similar manner trans-4-(3',4'-dimethoxy)benzyloxy-1-bromo-2-butene was also prepared: $^1$H NMR (400 MHz, CDCl$_3$) δ ppm 3.89 (s, 3H) 3.90 (s, 3H) 3.98 (d, 2H, J=8.0 Hz) 4.03 (d, 2H, J=8.0 Hz) 4.46 (s, 2H) 6.83-6.91 (m, 3H).

Reference Example 4

To a solution of [methoxy-Sar]$^3$-N-[trans-4-(3',4'-dimethoxy)benzyloxy-but-2-enyl]-Val$^5$-cyclosporine A (Compound 13) (0.32 g) in dry dichloromethane were added triethylamine (0.31 mL, 10 eq) and tert-butyldimethylsilyl trifluoromethanesulfonate (0.25 mL, 5.0 eq) at 0° C. and the resulting mixture was stirred at room temperature for 5 hours. It was diluted with dichloromethane, washed with water, saturated sodium chloride solution, and then concentrated under reduced pressure. The crude product was purified using flash silica gel column chromatography, eluting with a gradient of 0 to 80% ethyl acetate in heptane to yield [3'-tert-butyldimethylsiloxy-N-methyl-Bmt]$^1$-[methoxy-Sar]$^3$-N-[trans-4-(3',4'-dimethoxy)benzyloxy-but-2-enyl]-Val$^5$-cyclosporine A as a white solid; $^1$H NMR (400 MHz, DMSO-d$_6$) δ ppm −0.08 (s, 3H) 0.07 (s, 3H) 0.82 (s, 9H) 2.63 (s, 3H) 2.80 (s, 3H) 2.81 (s, 3H) 2.89 (s, 6H) 2.93 (s, 3H) 3.10 (s, 3H) 3.26 (s, 3H) 3.72 (s, 3H) 3.73 (s, 3H) 5.82-5.89 (m, 1H) 5.95 (s, 1H) 6.67 (d, 1H) 6.78-6.90 (m, 3H) 7.66 (d, 1H) 8.48 (d, 1H); mass spectra: 806.2 (M+Na)/2.

Reference Example 5

To a solution of [3'-tert-butyldimethylsiloxy-N-methyl-Bmt]$^1$-[methoxy-Sar]$^3$-N-[trans-4-(3',4'-dimethoxy)benzyloxy-but-2-enyl]-Val$^5$-cyclosporine A (0.29 g) in a solvent mixture of dichloromethane and water was added 2,3-dichloro-5,6-dicyano-p-benzoquinone (DDQ) (50 mg) and the resulting mixture was stirred at room temperature for 2 hours. It was diluted with dichloromethane, washed with saturated sodium bicarbonate solution, saturated sodium chloride solution, and then concentrated under reduced pressure. The crude product was purified using flash silica gel column chromatography, eluting with a gradient of 0 to 100% ethyl acetate in heptane to yield of [3'-tert-butyldimethylsiloxy-N-methyl-Bmt]$^1$-[methoxy-Sar]$^3$-N-[trans-4-hydroxy-but-2-enyl]-Val$^5$-cyclosporine A as a white solid; $^1$H NMR (400 MHz, DMSO-d$_6$) δ ppm −0.09 (s, 3H) 0.07 (s, 3H) 0.81 (s, 9H) 2.61 (s, 3H) 2.80 (s, 3H) 2.82 (s, 3H) 2.88 (s, 3H) 2.90

(s, 3H) 2.91 (s, 3H) 3.10 (s, 3H) 3.26 (s, 3H) 5.75-5.84 (m, 1H) 5.96 (s, 1H) 6.73 (d, 1H) 7.70 (d, 1H) 8.46 (d, 1H); mass spectra: 730.5 (M+2Na)/2.

Reference Example 6

To a solution of [3'-tert-butyldimethylsiloxy-N-methyl-Bmt]$^1$-[methoxy-Sar]$^3$-N-[trans-4-hydroxy-but-2-enyl]-Val$^5$-cyclosporine A (0.23 g) in dichloromethane was added Dess-Martin periodinane (140 mg) and the resulting mixture was stirred at room temperature for 1 hour. It was diluted with dichloromethane, washed with 10% sodium thiosulfate solution, saturated sodium bicarbonate solution and brine. After solvent removal, 0.23 g of [3'-tert-butyldimethylsiloxy-N-methyl-Bmt]$^1$-[methoxy-Sar]$^3$-N-[but-2-en-4-al]-Val$^5$-cyclosporine A was obtained, which was used without further purification; $^1$H NMR (400 MHz, DMSO-d$_6$) δ ppm –0.07 (s, 3H) 0.08 (s, 3H) 0.82 (s, 9H) 2.66 (s, 3H) 2.82 (s, 3H) 2.83 (s, 3H) 2.89 (s, 3H) 2.92 (s, 3H) 2.94 (s, 3H) 3.09 (s, 3H) 3.28 (s, 3H) 5.95 (s, 1H) 6.13-6.19 (m, 1H) 6.75 (d, 1H) 6.86-6.93 (m, 1H) 7.57 (m, 1H) 8.48 (d, 1H) 9.45 (d, 1H).

Reference Example 7

A mixture of iron pentacarbonyl (0.76 g, 3.90 mmol) and sodium hydroxide (80 mg, 1.95 mmol) in a 95:5 v/v solvent mixture of methanol and water was flushed with an inert gas and stirred at room temperature for 20 minutes to ensure complete depletion of sodium hydroxide. To this mixture was added a solution of [3'-tert-butyldimethylsiloxy-N-methyl-Bmt]$^1$-[methoxy-Sar]$^3$-N-[but-2-en-4-al]-Val$^5$-cyclosporine A (0.23 g) in the same solvent mixture and the resulting mixture was stirred at room temperature for 72 hours under an inert gas. The reaction mixture was poured into water and diethyl ether was added. The mixture was cooled to 0° C. and with stirring, iron (III) chloride was added until no gas evolution was observed. The layers were separated and the organic layer was washed with saturated NaHCO$_3$, brine and dried over anhydrous sodium sulfate. After solvent removal, the crude product was purified using flash silica gel column chromatography, eluting with a gradient of 0 to 100% ethyl acetate in heptane to yield 185 mg of [3'-tert-butyldimethylsiloxy-N-methyl-Bmt]$^1$-[methoxy-Sar]$^3$-N-[butan-4-al]-Val$^5$-cyclosporine A as a white solid; $^1$H NMR (400 MHz, DMSO-d$_6$) δ ppm –0.12 (s, 3H) 0.05 (s, 3H) 0.80 (s, 9H) 2.76 (s, 3H) 2.81 (s, 3H) 2.83 (s, 6H) 2.88 (s, 3H) 3.14 (s, 3H) 3.20 (s, 3H) 6.03 (s, 1H) 7.19 (d, 1H) 7.89 (m, 1H) 8.29 (d, 1H) 9.63 (m, 1H).

Reference Example 8

To a solution of [3'-tert-butyldimethylsiloxy-N-methyl-Bmt]$^1$-[methoxy-Sar]$^3$-N-[butan-4-al]-Val$^5$-cyclosporine A (0.09 g) in dry methanol was added sodium borohydride (4.8 mg, 2.0 eq) and the resulting mixture was stirred at room temperature for 1 hour. The reaction mixture was quenched with water and extracted with ethyl acetate. The organic layer was washed with brine and dried over anhydrous sodium sulfate. After solvent removal, 0.09 g of [3'-tert-butyldimethylsiloxy-N-methyl-Bmt]$^1$-[methoxy-Sar]$^3$-N-[4-hydroxybutyl]-Val$^5$-cyclosporine A was obtained, which was used without further purification; $^1$H NMR (400 MHz, DMSO-d$_6$) δ ppm –0.13 (s, 3H) 0.05 (s, 3H) 0.80 (s, 9H) 2.78 (s, 3H) 2.81 (s, 3H) 2.82 (s, 3H) 2.83 (s, 3H) 2.89 (s, 3H) 3.14 (s, 3H) 3.20 (s, 3H) 6.03 (s, 1H) 7.10 (d, 1H) 7.90 (d, 1H) 8.31 (d, 1H); mass spectra: 731.5 (M+2Na)/2.

Reference Example 9

To a solution of [3'-tert-butyldimethylsiloxy-N-methyl-Bmt]$^1$-[methoxy-Sar]$^3$-N-[butan-4-al]-Val$^5$-cyclosporine A (0.09 g) in dry methanol containing 0.01 ml of acetic acid was added dimethylamine (0.08 mL, 0.18 mmol, 2.0 M solution in THF) and sodium cyanoborohydride (10 mg, 0.14 mmol) and the resulting mixture was stirred at room temperature for 12 hour. It was then concentrated under reduced pressure and the residue was purified using flash silica gel column chromatography, eluting with a gradient of 0 to 70% of solvent B (B=DCM/MeOH/NH$_4$OH (90:9:1, v/v/v) in solvent A (A=DCM) to yield 85 mg of [3'-tert-butyldimethylsiloxy-N-methyl-Bmt]$^1$-[methoxy-Sar]$^3$-N-[4-dimethylaminobutyl]-Val$^5$-cyclosporine A as a white solid; $^1$H NMR (400 MHz, DMSO-d$_6$) δ ppm –0.12 (s, 3H) 0.06 (s, 3H) 0.80 (s, 9H) 2.07 (s, 6H) 2.80 (s, 3H) 2.81 (s, 3H) 2.82 (s, 3H) 2.83 (s, 3H) 2.89 (s, 3H) 3.13 (s, 3H) 3.21 (s, 3H) 6.02 (s, 1H) 7.06 (d, 1H) 7.86 (d, 1H) 8.31 (d, 1H); mass spectra: 723.7 (M+2H)/2.

[(R)-Methoxy-Sar]$^3$ cyclosporine A (also known as 3-methoxycyclosporine A) is described in U.S. Pat. No. 6,583,265 and PCT Publication No. WO2006/0398668, the contents of which are incorporated herein by reference in their entirety.

HCV Activity

Representative compounds of the present invention were tested for activity against HCV using the methods adapted from those described by Kriger et al., 2001, *Journal of Virology* 75:4614-4624, Pietschmann et al., 2002, *Journal of Virology*, 76:4008-4021, and using HCV RNA constructs as described in U.S. Pat. No. 6,630,343. Compounds were examined in the human hepatoma cell line ET (lub ubi neo/ET), a HCV RNA replicon containing a stable luciferase (LUC) reporter. The HCV RNA replicon ET contains the 5' end of HCV (with the HCV Internal Ribosome Entry Site (IRES) and the first few amino acids of the HCV core protein) which drives the production of a firefly luciferase (LUC), ubiquitin, and neomycin phosphotransferase (NeoR) fusion protein. Ubiquitin cleavage releases the LUC and NeoR proteins. The EMCV IRES element controls the translation of the HCV structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The activity of the LUC reporter is directly proportional to HCV replication levels and positive-control antiviral compounds produce a reproducible antiviral response using the LUC endpoint.

The compounds were dissolved in DMSO at five half-log concentrations each, ranging from either 0.03 to 3 µM or 1 to 100 µM. Subconfluent cultures of the ET line were plated out into 96 well plates dedicated for the analysis of cell numbers (cytotoxicity) or antiviral activity and the next day the compounds were added to the appropriate wells. The cells were processed 72 hours later when the cells were still subconfluent. Antiviral activity was expressed as EC$_{50}$ and EC$_{90}$, the effective concentration of compound that reduced viral replication by 50% and 90%, respectively. Compound EC$_{50}$ and EC$_{90}$ values were derived from HCV RNA levels assessed as HCV RNA replicon derived LUC activity. Cytotoxicity was expressed as IC$_{50}$ and IC$_{90}$, the concentration of compound that inhibited cell viability by 50% and 90%, respectively. Compound IC$_{50}$ and IC$_{90}$ values were calculated using a colorimetric assay as an indication of cell numbers and cytotoxicity. The activity of the LUC reporter is directly proportional to HCV RNA levels in the human cell line. The HCV-replicon assay was validated in parallel experiments using interferon-alpha-2b as a positive control. Cyclosporine was also tested by way of comparison. Representative compounds disclosed herein inhibited HCV replication in human liver cells. In particular, Compound Nos. 1 to 4, 6 to 12, 14 to 17, 20 and 21 had EC$_{50}$ value of less than 1000 nM. Compound 5 had an EC$_{50}$ value greater than 1000 nM. In addition, when considering the level of cytotoxicity, such compounds exhibited a safety margin (antiviral IC$_{50}$ versus cytotoxicity EC$_{50}$).

Cyclophilin Binding Activity

The cyclophilin inhibition binding of compounds disclosed herein is determined using a competitive ELISA adapted from the methods described by Quesniaux et al. (*Eur. J. Immunol.*, 1987, 17:1359-1365). Activated ester of succinyl spacers bound to D-Lys$^8$-cyclosporine A (D-Lys$^8$-Cs) are coupled to bovine serum albumin (BSA) through D-lysyl residue in position 8. BSA is dissolved in 0.1 M borate buffer, pH 9.0 (4 mg in 1.4 ml). A hundredfold molar excess of D-Lys$^8$-Cs dissolved in dimethyl formamide (0.6 ml) is added drop wise to the BSA under vigorous stirring. The coupling reaction is performed for 2 to 3 hours at room temperature under mild stirring and the conjugate is extensively dialyzed against phosphate-buffered saline (PBS, pH 7.4). After acetone precipitation of an aliquot of the conjugated protein, no covalently bound D-Lys$^8$-Cs remains in the acetone solution and the extent of cyclosporine covalent binding is calculated.

Microtiter Plates are coated with D-Lys$^8$-Cs-BSA conjugate (2 μg/ml in PBS for 24 hours at 4° C.). Plates are washed with Tween®/PBS and with PBS alone. To block nonspecific binding, 2% BSA/PBS (pH 7.4) is added to the wells and allowed to incubate for 2 hours at 37° C. A five-fold dilution series of the compound to be tested is made in ethanol in a separate microtiter plate. The starting concentration is 0.1 mg/mL for assays with human recombinant cyclophilin. 198 μL of 0.1 μg/mL cyclophilin solution is added to the microtiter immediately followed by 2 μL of diluted cyclosporine A (used as a reference compound) or the compound of the invention. The reaction between coated BSA-Cs conjugate, free cyclosporine A and cyclophilin is allowed to equilibrate overnight at 4° C. Cyclophilin is detected with anti-cyclophilin rabbit antiserum diluted in 1% BSA containing PBS and incubates overnight at 4° C. Plates are washed as described above. Bound rabbit antibodies are then detected by goat anti-rabbit IgG conjugated to alkaline phosphatase diluted in 1% BSA-PBS and allowed to incubate for 2 hours at 37° C. Plates are washed as described above. After incubation with 4-nitrophenyl phosphate (1 g/l in diethanolamine buffer, pH 9.8) for 1 to 2 hours at 37° C., the enzymatic reaction is measured spectrophotometrically at 405 nm using a spectrophotometer. The results are expressed as an EC$_{50}$, which is the concentration of the compound of the invention required to achieve 50% inhibition. Compounds 1 to 4, 6 to 17, 20 and 21 had EC$_{50}$ values of less than 600 nM against cyclophilins A and B; Compound 5 had an EC$_{50}$ value of greater than 600 nM against cyclophilins A and B. Compound Nos. 1 to 3, 6 to 12, 14 to 17 and 21 had EC$_{50}$ values of less than 600 nM against cyclophilin D; Compound Nos. 4, 5 and 20 had EC$_{50}$ values of greater than 600 nM against cyclophilin D.

Compounds disclosed herein are tested for their T Cell stimulation (IL-2) in Jurkat cells with anti-CD3 and anti-CD28 co-stimulation. All compounds have a 0.5-Log 9-point titration starting at 10 μM (n=2) to 0.0015 μM. Cyclosporine A (control) is also run at a 0.5-Log 9-point titration starting at 500 ng/mL. All compounds to be tested are dissolved in dimethyl sulfoxide. Cytotoxicity is evaluated with parallel Alamar Blue plates. Jurkat cells are seeded at 2×10$^5$ cells per well in 190 μL growth media in a 96-well plate. Cells are cultured in RPMI 1640 medium, 10% fetal bovine serum, and L-Glutamine with incubation at 37° C. with 5% carbon dioxide. After 1 hour of incubation the cells are stimulated with immobilized anti-CD3 (0.4 μg/well), anti-CD28 soluble (2 μg/mL). After 6 hours the sample supernatants are harvested and stored at −80° C. 50 μL samples of supernatant are tested for IL-2 using a Luminex® I-plex assay.

Mitochondrial Permeability Transition

Mitochondrial Permeability Transition (MPT) is determined by measuring swelling of the mitochondria induced by Ca$^{2+}$. The procedure is adapted from the method described by Blattner et al., 2001, *Analytical Biochem*, 295:220. Mitochondria are prepared from rat livers, which have been perfused with phosphate-buffered saline (PBS) to remove blood, using standard methods that utilize gentle homogenization in sucrose based buffer and then differential centrifugation to first remove cellular debris and then to pellet the mitochondria. Swelling is induced by 150 micro molar Ca$^{2+}$ (added from a concentrated solution of CaCl$_2$) and is monitored by measuring the scattering at 535-540 nm. Representative compounds are added 5 minutes before swelling is induced. EC$_{50}$ is determined by comparing swelling with and without the compounds disclosed herein. Compound Nos. 1, 6 to 11, 14, 16, 20 and 21 had EC$_{50}$ values of less than 10 μm; Compound Nos. 2 to 5 had EC$_{50}$ values of greater than 10 μm; Compound Nos. 12 and 17 had EC$_{50}$ values of greater than 1.5 μm.

All publications and patent applications cited in this specification are herein incorporated by reference as if each individual publication or patent application were specifically and individually indicated to be incorporated by reference. While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What we claim is:

1. A compound of formula (I):

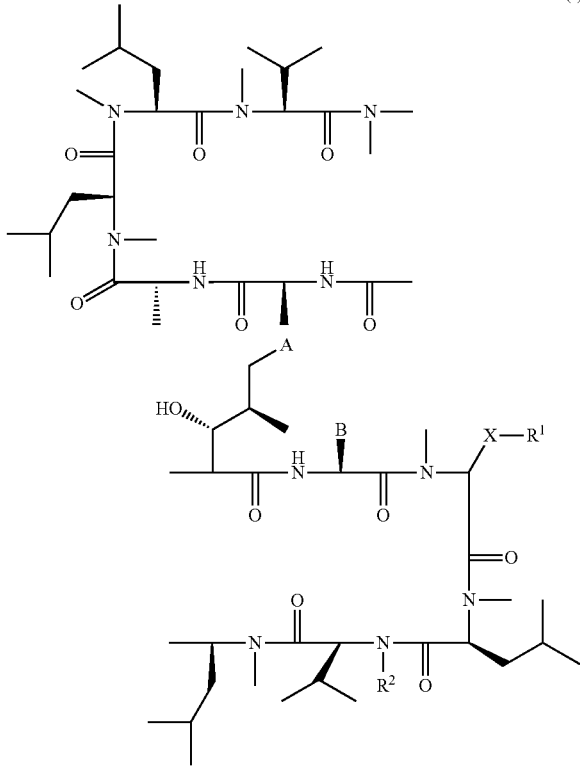

wherein:

A represents (E) —CH=CHR, wherein R represents methyl;

B represents ethyl;

$R^1$ represents:
straight- or branched-chain alkyl containing from one to six carbon atoms, optionally substituted by one or more groups $R^3$ which may be the same or different;

$R^2$ represents:
straight- or branched-chain alkyl containing from one to six carbon atoms, substituted by one or more groups $R^{41}$ which may be the same or different; or
straight- or branched-chain alkenyl containing from two to six carbon atoms, substituted by one or more groups $R^{42}$ which may be the same or different;

X represents oxygen or sulfur;

$R^3$ represents amino, N-alkylamino, N,N-dialkylamino or cycloalkyl;

$R^{41}$ represents:
halogen, hydroxyl, alkoxy, —$OR^8$, carboxyl, alkoxycarbonyl, —$NR^5R^6$, —$NR^7(CH_2)_mNR^5R^6$, formyl, —C(=O)$R^8$, —S(O)$_pR^8$; phenyl substituted by from one to five groups which may be the same or different selected from the group consisting of alkyl, haloalkyl, hydroxyl, alkoxy, amino, N-alkylamino, N,N-dialkylamino, carboxyl and alkoxycarbonyl; or
cycloalkyl containing from three to six carbon atoms optionally substituted by one or more groups which may be the same or different selected from the group consisting of halogen, hydroxyl, amino, N-monoalkylamino and N,N-dialkylamino;
or $R^{41}$ represents a carbon-linked saturated or unsaturated heterocyclic ring containing from four to six ring atoms, which ring contains from one to three heteroatoms which may be the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino and N,N-dialkylamino;

$R^{42}$ represents:
halogen, hydroxyl, —$NR^5R^6$, —$OR^8$, carboxyl, alkoxycarbonyl, —C(=O)$NR^5R^6$, formyl, —C(=O)$R^8$, —S(O)$_nR^8$, —$NR^7(CH_2)_mNR^5R^6$;
phenyl substituted by from one to five groups which may be the same or different selected from the group consisting of alkyl, haloalkyl, hydroxyl, alkoxy, amino, N-alkylamino, N,N-dialkylamino, carboxyl and alkoxycarbonyl; or
cycloalkyl containing from three to six carbon atoms optionally substituted by one or more groups which may be the same or different selected from the group consisting of halogen, hydroxyl, amino, N-monoalkylamino and N,N-dialkylamino;
or $R^{42}$ is a carbon-linked saturated or unsaturated heterocyclic ring containing from four to six ring atoms, which ring contains from one to three heteroatoms which may be the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino and N,N-dialkylamino;

$R^5$ and $R^6$, which may be the same or different, each represent:
hydrogen; straight- or branched-chain alkyl containing from one to six carbon atoms;
straight- or branched-chain alkenyl or alkynyl containing from two to four carbon atoms; or
cycloalkyl containing from three to six carbon atoms optionally substituted by straight- or branched-chain alkyl containing from one to six carbon atoms;
or $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, phenyl and benzyl;

$R^7$ represents hydrogen, straight- or branched-chain alkyl containing from one to six carbon atoms, cyano or alkylsulfonyl;

$R^8$ represents:
straight- or branched-chain alkyl containing from one to six carbon atoms;
aryl optionally substituted by from one to five groups which may be the same or different selected from the group consisting of alkyl, haloalkyl, halogen, hydroxyl, alkoxy, amino, N-alkylamino and N,N-dialkylamino;
heteroaryl optionally substituted by from one to five groups which may be the same or different selected from the group consisting of alkyl, haloalkyl, halogen, hydroxyl, alkoxy, amino, N-alkylamino and N,N-dialkylamino;
aralkyl, wherein the aryl ring is optionally substituted by from one to five groups which may be the same or different selected from the group consisting of halogen, amino, N-alkylamino, N,N-dialkylamino, alkoxy and haloalkyl, wherein the alkyl contains one to three carbon atoms; or
heteroarylalkyl wherein the heteroaryl ring is optionally substituted by halogen, amino, N-alkylamino, N,N-dialkylamino, alkoxy and haloalkyl, wherein the alkyl contains one to three carbon atoms;

m is an integer from one to four;

n is an integer of zero, one or two; and p is an integer of zero, one or two;

or a pharmaceutically acceptable salt thereof.

2. The compound according to claim 1 wherein:

$R^2$ represents:
straight- or branched-chain alkyl containing from one to six carbon atoms, substituted by one or more groups $R^{41}$ which may be the same or different; or
straight- or branched-chain alkenyl containing from two to six carbon atoms, substituted by one or more groups $R^{42}$ which may be the same or different;

$R^{41}$ represents:
halogen, hydroxyl, alkoxy, carboxyl, alkoxycarbonyl, —$NR^5R^6$, —$NR^7(CH_2)_mNR^5R^6$; or
phenyl substituted by from one to five groups which may be the same or different selected from the group consisting of alkyl, haloalkyl, hydroxyl, alkoxy, amino, N-alkylamino, N,N-dialkylamino, carboxyl and alkoxycarbonyl;
or $R^{41}$ represents a carbon-linked saturated or unsaturated heterocyclic ring containing from four to six ring atoms, which ring contains one or two heteroatoms which may the same or different selected from the group consisting of nitrogen, oxygen and sulfur, which ring may be optionally substituted by from one to four groups which may be the same or different selected from the group consisting of alkyl, halogen, alkoxy, amino, carboxyl and alkyl, which alkyl is substituted by amino, N-alkylamino and N,N-dialkylamino;

$R^{42}$ represents halogen, hydroxyl, amino, N-monoalkylamino or N,N-dialkylamino;

$R^5$ and $R^6$, which may be the same or different, each represent:
hydrogen;
straight- or branched-chain alkyl containing from one to six carbon atoms;
straight- or branched-chain alkenyl or alkynyl containing from two to four carbon atoms; or
cycloalkyl containing from three to six carbon atoms optionally substituted by straight- or branched-chain alkyl containing from one to six carbon atoms;
or $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen, oxygen and sulfur, which ring may be optionally substituted by from one to four groups which may be the same or different selected from the group consisting of alkyl, phenyl and benzyl;

$R^7$ represents hydrogen, straight- or branched-chain alkyl containing from one to six carbon atoms, cyano or alkylsulfonyl; and m is an integer from one to four.

3. The compound according to claim 1 wherein $R^{41}$ represents hydroxyl, —$NR^5R^6$, $OR^8$, carboxyl, alkoxycarbonyl, -formyl or —C(=O)$R^8$; and $R^{42}$ represents hydroxyl, —$NR^5R^6$, —$OR^8$, carboxyl, alkoxycarbonyl, —C(=O)$NR^5R^6$, formyl or —C(=O)$R^8$.

4. The compound according to claim 1 which is selected from the group consisting of:
[(R)-2-(N,N-dimethylamino)ethylthio-Sar]$^3$-(4-isopropylbenzyl)-Val$^5$-cyclosporine A;
[methoxy-Sar]$^3$-(3-trifluoromethylbenzyl)-Val$^5$-cyclosporine A;
[methoxy-Sar]$^3$-(N-but-2-enyl)-Val$^5$-cyclosporine A;
[methoxy-Sar]$^3$-(N-3-methyl-but-2-enyl)-Val$^5$-cyclosporine A;
[methoxy-Sar]$^3$-N-(trans-4-benzyloxy-but-2-enyl)-Val$^5$-cyclosporine A;
[methylthio-Sar]$^3$-N-[trans-4-(3',4'-dimethoxy)benzyloxy-but-2-enyl]-Val$^5$-cyclosporine A;
[methoxy-Sar]$^3$-N-[trans-4-(3',4'-dimethoxy)benzyloxy-but-2-enyl]-Val$^5$-cyclosporine A;
[methylthio-Sar]$^3$-N-[trans-4-hydroxy-but-2-enyl]-Val$^5$-cyclosporine A;
[methoxy-Sar]$^3$-N-[trans-4-hydroxy-but-2-enyl]-Val$^5$-cyclosporine A;
[methylthio-Sar]$^3$-N-[trans-4-dimethylamino-but-2-enyl]-Val$^5$-cyclosporine A;
[methoxy-Sar]$^3$-N-[trans-4-dimethylamino-but-2-enyl]-Val$^5$-cyclosporine A;
[methoxy-Sar]$^3$-N-[4-hydroxybutyl]-Val$^5$-cyclosporine A; and
[methoxy-Sar]$^3$-N-[4-dimethylaminobutyl]-Val$^5$-cyclosporine A;
or a pharmaceutically acceptable salt thereof.

5. A composition comprising a compound of formula (I) as defined in claim 1, or a pharmaceutically acceptable salt thereof, and a pharmaceutically acceptable excipient, carrier or diluent.

* * * * *